United States Patent
Novak et al.

(10) Patent No.: US 11,672,907 B2
(45) Date of Patent: Jun. 13, 2023

(54) FILTER FOR REDUCING PHENOLIC COMPOUNDS FROM INSULIN AND RELATED INFUSION AND INJECTION DEVICES

(71) Applicant: Becton, Dickinson and Company, Franklin Lakes, NJ (US)

(72) Inventors: Matthew Novak, Oakland, CA (US); Alfred J. Harvey, Raleigh, NC (US); Douglas B. Sherman, Durham, NC (US); Robert J. Radford, Skokie, IL (US); Javier Alarcon, Durham, NC (US); Ronald J. Pettis, Cary, NC (US); Kelly Magee Riley, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 843 days.

(21) Appl. No.: 16/609,657

(22) PCT Filed: May 1, 2018

(86) PCT No.: PCT/US2018/030400
§ 371 (c)(1),
(2) Date: Oct. 30, 2019

(87) PCT Pub. No.: WO2018/204327
PCT Pub. Date: Nov. 8, 2018

(65) Prior Publication Data
US 2020/0147300 A1    May 14, 2020

Related U.S. Application Data

(60) Provisional application No. 62/636,405, filed on Feb. 28, 2018, provisional application No. 62/492,443, filed on May 1, 2017.

(51) Int. Cl.
A61M 5/165 (2006.01)
A61M 5/31 (2006.01)

(52) U.S. Cl.
CPC .......... *A61M 5/165* (2013.01); *A61M 5/3145* (2013.01); *A61M 2205/759* (2013.01)

(58) Field of Classification Search
CPC ................ A61M 5/165; A61M 5/3145; A61M 2205/759
See application file for complete search history.

(56) References Cited

U.S. PATENT DOCUMENTS 2,571,059 A    10/1951 Puschelberg et al.
4,263,407 A     4/1981 Reed, Jr.
(Continued)

FOREIGN PATENT DOCUMENTS

CN    101687150 A    3/2010
EP     2164614 A2    3/2010
(Continued)

OTHER PUBLICATIONS

Chinese Office Action dated Apr. 2, 2021, which issued in the corresponding Chinese Patent Application No. 201880029078.2, including Eng. translation.
(Continued)

*Primary Examiner* — Amber R Stiles
(74) *Attorney, Agent, or Firm* — Dickinson Wright PLLC

(57) ABSTRACT

Provided herein are devices, systems, and methods for the removal of preservatives/excipients/stabilizers from pharmaceutical preparations/medicaments. The devices and systems include a resin for the filtering of preservatives from pharmaceutical preparations. The methods allow for a period of time of incubation of the pharmaceutical preparation in the resin that effectively removes preservatives, while at the same time maintaining the required amount or con- (Continued)

centration of active compound in the preparation. Also provided herein are devices, systems, and methods for the controlled release of anti-inflammatory agents in an insulin infusion set.

26 Claims, 18 Drawing Sheets

(56) References Cited

U.S. PATENT DOCUMENTS

| | | | |
|---|---|---|---|
| 5,936,061 A * | 8/1999 | Andersson | C07K 14/61 |
| | | | 530/427 |
| 2007/0102358 A1 * | 5/2007 | Good | G01N 30/6017 |
| | | | 422/400 |
| 2008/0314836 A1 | 12/2008 | Leach et al. | |
| 2012/0053364 A1 * | 3/2012 | Leach | B01J 20/103 |
| | | | 562/577 |
| 2016/0354542 A1 | 12/2016 | Ward et al. | |

FOREIGN PATENT DOCUMENTS

| | | |
|---|---|---|
| JP | S55-18297 A | 2/1980 |
| JP | H11-514920 A | 12/1999 |
| JP | 2010-531167 A1 | 9/2010 |
| JP | 2018-568190 A | 4/2019 |
| WO | 200112746 A1 | 2/2001 |
| WO | 2009002794 A2 | 12/2008 |
| WO | 2017/184985 A1 | 10/2017 |

OTHER PUBLICATIONS

International Search Report dated Aug. 14, 2018, which issued in the corresponding PCT Patent Application No. PCT/US2018/030400.

* cited by examiner

FILTER FOR REDUCING PHENOLIC COMPOUNDS FROM INSULIN AND RELATED INFUSION AND INJECTION DEVICES

CROSS-REFERENCE TO RELATED APPLICATIONS

This application claims priority to U.S. Provisional Application No. 62/492,443, filed May 1, 2017 and titled "Filter for Reducing Phenolic Compounds From Insulin and Related Infusion and Injection Devices", and U.S. Provisional Application No. 62/636,405, filed on Feb. 28, 2018 and titled "Filter for Reducing Phenolic Compounds From Insulin and Related Infusion and Injection Devices", the disclosures of which are both incorporated herein by reference in their entirety.

BACKGROUND OF THE INVENTION

Field of the Invention

The present disclosure relates generally to devices, systems, and methods for the filtering of pharmaceutical compositions prior to administration. More particularly, the present disclosure relates to devices, systems, and methods for removal of preservatives, stabilizers, and other excipients from pharmaceuticals such as insulin by interaction of the pharmaceutical with one or more resins prior to administration. The present application also relates to devices, systems, and methods for the controlled release of anti-inflammatory agents in an insulin infusion or injection set.

Description of Related Art

A wide variety of pharmaceuticals or medicaments are prepared, in bulk, to have long shelf lives. This advantage is achieved through the use of preservatives, such as stabilizers, and other excipients included in the pharmaceutical/medicament preparation. By way of example, commercial insulin preparations can include phenols and phenolic derivatives, such as m-cresol, to stabilize a hexameric form of insulin, which normally exists in a monomeric form, in the pharmaceutical solution, allowing for extended shelf life of the product.

However, the preservatives included in the pharmaceutical/medicament are often toxic to cells, and can induce release of pro-inflammatory cytokines and/or chemokines, leading to inflammatory responses in individuals, particularly in circumstances, such as insulin, where the preservative-filled medicament is administered repeatedly. Current commercially available insulin infusion sets are limited by a useful life of three days, after which time patients begin to experience altered pharmacokinetic and pharmacodynamics profiles, adverse tissue reactions, and loss of glycemic control. For example, phenolic and m-cresol preservatives often used in commercial insulin preparations can induce an increase in interleukin-6 levels. These increased levels of pro-inflammatory cytokines can lead to adverse events. Additionally, these deleterious reactions are dose-dependent, so as more excipient is delivered (as would be found in a real life infusion scenario), pharmacokinetics are increasingly altered relative to initial values. The problems associated with phenolic excipients of insulin formulations are detailed in "Phenolic excipients of insulin formulations induce cell death, pro-inflammatory signaling and MCP-1 release", C. Weber, D. Kammerer, B. Streit, A. Licht, Toxicology Reports 2, (2015) 194-202, available at www.elsevier.com/locate/toxrep, an incorporated herein by reference.

Previous efforts to remove the preservatives have involved the use of zeolites, for example by either providing the zeolite directly in the composition, or by passing the pharmaceutical solution over zeolites, for example in a column. However, use of zeolites is associated with significant drawbacks. Because zeolites work on the principal of size exclusion, not all preservatives can be reliably removed from the pharmaceutical/medicament. In addition, significant force is required to pass the pharmaceutical/medicament solution over the zeolites. Accordingly, there is a need in the art for devices, systems, and methods that provide comprehensive and simple filtering of preservatives from pharmaceuticals/medicaments.

Beyond excipient-induced tissue reaction, conventional extended wear devices, such as insulin infusion sets, are also disadvantaged by device biocompatibility. Any device implanted for an extended period of time, such as more than three days, tends to induce a separate device-associated inflammation at the site of administration. This device-associated inflammatory mechanism alters subcutaneous insulin pharmacokinetics. The combination of device-induced and excipient-induced modes of inflammation negatively impact device performance, thereby limiting wear time of the device, typically to a period of three days.

SUMMARY OF THE INVENTION

The present disclosure provides a filtering device for removing a preservative from a pharmaceutical composition. The filtering device includes a body having at least one inlet and at least one outlet and defining a fluid flow channel provided between the at least one inlet and at least one outlet, the fluid flow channel being in fluid communication with at least one chamber. The device also includes at least one resin disposed in the at least one chamber and at least one filter disposed in the fluid flow channel.

In accordance with an embodiment of the present invention, the filtering device is for filtering preservatives from insulin. In certain configurations, the preservative is a phenolic compound or derivative thereof.

In accordance with an embodiment of the present invention, the resin includes a nonpolar compound. In certain configurations, the resin includes a polystyrene. In certain configurations, the resin is polystyrene. In certain configurations, the resin includes a plurality of porous polystyrene-divinyl-benzene beads. In certain configurations, the porous polystyrene-divinyl-benzene beads have a pore diameter of less than about 100 Å. In certain other configurations, the resin is a carbonaceous material.

In accordance with an embodiment of the present invention, the filtering device includes a second filter, the first filter and second filter provided in the fluid flow channel on opposing sides of the chamber. In certain configurations, at least the first filter has a pore size of between about 15 μm and about 45 μm.

In accordance with an embodiment of the present invention, the filtering device further includes a needle disposed at the outlet, the needle being in fluid communication with the fluid flow channel. In certain configurations, the filter at least partially removes metal ion excipients from the pharmaceutical composition.

The present disclosure also provides a system including an infusion or injection device for delivery of a pharmaceutical/medicament and a filtering device. The filtering device includes a body having at least one inlet and at least one outlet and defining a fluid flow channel provided between the at least one inlet and at least one outlet, the fluid flow channel being in fluid communication with at least one chamber. The device also includes at least one resin disposed in the at least one chamber and at least one filter disposed in the fluid flow channel.

In accordance with an embodiment of the present invention, the filtering device further includes a needle disposed at the outlet, the needle being in fluid communication with the fluid flow channel. In certain configurations, the filter at least partially removes metal ion excipients from the pharmaceutical composition. The present disclosure also provides a system including an infusion or injection device for delivery of a pharmaceutical/medicament and a filtering device. The filtering device includes a body having at least one inlet and at least one outlet and defining a fluid flow channel provided between the at least one inlet and at least one outlet, the fluid flow channel being in fluid communication with at least one chamber. The device also includes at least one resin disposed in the at least one chamber and at least one filter disposed in the fluid flow channel.

In accordance with an embodiment of the present invention, the infusion or injection device is a syringe, an autoinjector, a pen injector, or an infusion pump. In certain configurations, the at least one filter of the filtering device is located between the chamber and the outlet. In certain configurations, the infusion or injection device is attached to the inlet of the filtering device. In accordance with an embodiment of the present invention, the system includes a needle attached to the outlet of the filtering device. In certain configurations the needle is releasably attached to the outlet of the filtering device. In certain other configurations, the needle is permanently affixed to the outlet of the filtering device.

In accordance with an embodiment of the present invention, the infusion or injection device is a syringe, autoinjector, or pen injector and the filtering device includes at least two filters, one filter disposed in the fluid flow channel between the chamber and the inlet and one filter disposed in the fluid flow channel between the chamber and the outlet, and the filtering device includes a needle attached to the outlet.

In accordance with an embodiment of the present invention, the resin comprises a nonpolar compound. In certain configurations, the resin comprises a polystyrene. In certain configurations, the resin comprises polystyrene. In certain configurations, the resin comprises a plurality of porous polystyrene-divinyl-benzene beads. In certain configurations, the porous polystyrene-divinyl-benzene beads have a pore diameter of less than about 100 Å. In certain other configurations, the resin is a carbonaceous material.

The present disclosure also provides a method of filtering a preservative from a pharmaceutical composition. The method includes passing the composition through a filtering device including a body having at least one inlet and at least one outlet and defining a fluid flow channel provided between the at least one inlet and at least one outlet, the fluid flow channel being in fluid communication with at least one chamber. The filtering device also includes at least one resin disposed in the at least one chamber and at least one filter disposed in the fluid flow channel.

In accordance with an embodiment of the present invention, the method filters preservatives from insulin. In certain configurations, the preservative is a phenolic compound or derivative thereof.

In accordance with an embodiment of the present invention, the resin includes a nonpolar compound. In certain configurations, the resin includes a polystyrene. In certain configurations, the resin is polystyrene. In certain configurations, the resin includes a plurality of porous polystyrene-divinyl-benzene beads. In certain configurations, the porous polystyrene-divinyl-benzene beads have a pore diameter of less than about 100 Å. In certain other configurations, the resin is a carbonaceous material.

In accordance with an embodiment of the present invention, the filtering device used in the method is in fluid communication with an infusion or injection device such as a syringe, an autoinjector, a pen injector, or an infusion pump. In certain configurations, the infusion or injection device is attached to the inlet off the filtering device.

In accordance with an embodiment of the present invention, the at least one filter of the filtering device is located between the chamber and the outlet In accordance with an embodiment of the present invention, the filtering device includes a needle attached to the outlet. In certain configurations the needle is releasably attached to the outlet of the filtering device. In certain other configurations, the needle is permanently affixed to the outlet of the filtering device.

In accordance with an embodiment of the present invention, the infusion or injection device is a syringe, autoinjector, or pen injector and the filtering device includes at least two filters, one filter disposed in the fluid flow channel between the chamber and the inlet and one filter disposed in the fluid flow channel between the chamber and the outlet, and the filtering device includes a needle attached to the outlet.

The present invention also provides a system including an injection device including a housing defining a chamber configured to hold a medicament, a displaceable plunger rod disposed at least partially within the housing, and an outlet in fluid communication with the chamber. The system further includes a filtering device for removing a preservative from a pharmaceutical composition. The filtering device includes a body having at least one inlet and at least one outlet and defining a fluid flow channel provided between the at least one inlet and at least one outlet, the fluid flow channel being in fluid communication with at least one chamber. The device also includes at least one resin disposed in the at least one chamber and at least one filter disposed in the fluid flow channel. In the system of the present invention, the outlet of the injection device is attached to the inlet of the filtering device such that the chamber of the injection device is in fluid communication with the fluid flow channel of the filtering device.

In accordance with an embodiment of the present invention, the filtering device is removably attached to the injection device.

In accordance with an embodiment of the present invention, the injection device further includes an actuator and a spring disposed to advance the plunger rod upon actuation of the actuator and the filtering device further includes a needle attached to the outlet.

In accordance with an embodiment of the present invention, the plunger rod of the injection device is manually actuatable and the filtering device further includes a needle attached to the outlet.

In accordance with an embodiment of the present invention, the infusion or injection device is an infusion pump and the filtering device further includes a needle attached to the outlet.

In accordance with an embodiment of the present invention, the medicament in the chamber of the injection device is insulin.

In accordance with an embodiment of the present invention, the resin of the filtering device includes a nonpolar compound. In certain configurations, the resin includes a polystyrene. In certain configurations, the resin is polystyrene. In certain configurations, the resin includes a plurality of porous polystyrene-divinyl-benzene beads. In certain configurations, the porous polystyrene-divinyl-benzene beads have a pore diameter of less than about 100 Å. In certain other configurations, the resin is a carbonaceous material.

In accordance with an embodiment of the present invention, an infusion set for delivering a pharmaceutical composition may have a tubing with a proximal end and a distal end, a needle in fluid communication with the distal end of the tubing, and a dermal pad having an adhesive. At least one of the needle or the dermal pad may have an anti-inflammatory agent. At least a portion of an interior surface and/or exterior surface of the needle may have a coating having the anti-inflammatory agent. A bottom surface of the dermal pad may have an adhesive having the anti-inflammatory agent. The infusion set may further have a connector at the proximal end of the tubing for connecting to an infusion device. The connector may be a threaded connector. The anti-inflammatory agent may be a steroidal or non-steroidal anti-inflammatory agent. The infusion set may further have an infusion device, such as an infusion pump.

In accordance with an embodiment of the present invention, the infusion set may further have a filtering device for removing a preservative from a pharmaceutical composition. The filtering device may have a body having at least one inlet and at least one outlet and defining a fluid flow channel provided between the at least one inlet and at least one outlet, the fluid flow channel being in fluid communication with at least one chamber. At least one resin may be disposed in the at least one chamber, and at least one filter may be disposed in the fluid flow channel. The pharmaceutical composition may be insulin. The preservative may be a phenolic compound or derivative thereof. The resin may have a nonpolar compound, polystyrene, divinyl benzene, or a plurality of porous polystyrene-divinyl-benzene beads. The porous polystyrene-divinyl-benzene beads may have a pore diameter of less than about 100 Å. The resin may have a carbonaceous material. The at least one filter may have a pore size of between about 15 μm and about 45 μm.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

DETAILED DESCRIPTION OF THE INVENTION

Figure 1:
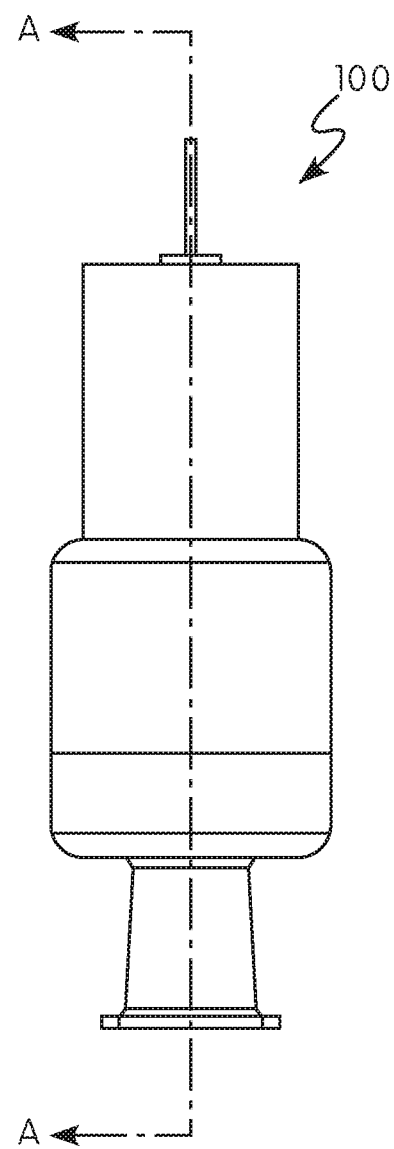
FIG. 1 is a schematic and cross-sectional representation (taken along line A-A) of a filtering device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

As used herein, the singular form of "a", "an", and "the" include plural referents unless the context clearly dictates otherwise.

Spatial or directional terms, such as "left", "right", "inner", "outer", "above", "below", and the like, relate to the invention as shown in the drawing figures and are not to be considered as limiting as the invention can assume various alternative orientations.

All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

The term "at least" is synonymous with "greater than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes A alone; or B alone; or C alone; or A and B; or A and C; or B and C; or all of A, B, and C.

The term "adjacent" means proximate to but not in direct contact with.

The term "includes" is synonymous with "comprises".

As used herein, the terms "parallel" or "substantially parallel" mean a relative angle as between two objects (if extended to theoretical intersection), that is from 0° to 5°, or from 0° to 3°, or from 0° to 2°, or from 0° to 1°, or from 0° to 0.5°, or from 0° to 0.25°, or from 0° to 0.1°, inclusive of the recited values.

As used herein, the terms "perpendicular" or "substantially perpendicular" mean a relative angle as between two objects at their real or theoretical intersection is from 85° to 90°, or from 87° to 900, or from 88° to 90°, or from 89° to 90°, or from 89.5° to 90°, or from 89.75° to 90°, or from 89.9° to 90°, inclusive of the recited values.

Figure 2:
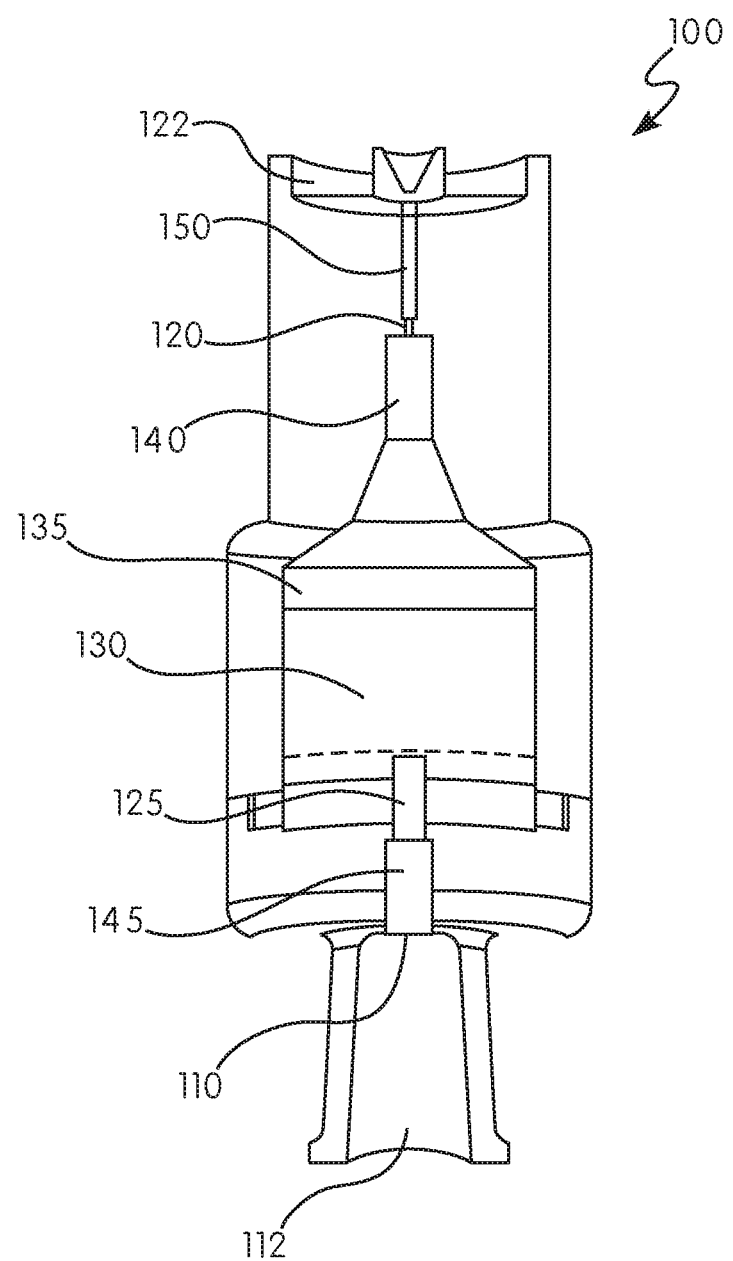
FIG. 2 is a schematic and cross-sectional representation (taken along line A-A) of a filtering device in accordance with an embodiment of the present invention.

FIGS. 1 and 2 illustrate an exemplary embodiment of a filtering device 100 of the present disclosure, including a cross-section view along line A-A. The filtering device 100 includes an inlet 110 and an outlet 120, and a fluid flow channel 125 extending between the inlet 110 and the outlet 120. The fluid flow channel 125 is in fluid communication with, at least one chamber 130 disposed within the body of the filtering device 100. The chamber 130 includes a resin 135 therein, the resin provided for the filtering or removal of preservatives, excipients, or stabilizers included in a pharmaceutical or medicament. The filtering device 100 further includes at least one filter 140 disposed in the fluid flow channel 125 between the chamber 130 holding resin 135 and the outlet 120. The device can be configured with a connection 112 to allow attachment to a medical device, such as an injector or pen. In one embodiment, the connection is a luer connection (male or female). In another embodiment, the device can include features to aid in the delivery of the pharmaceutical or medicament 122, such as a tissue displacement zone.

A device as described herein can include a needle 150. The needle 150 can be disposed at any useful location on the filtering device, whether in the fluid flow channel 125 or externally at or near outlet 120, so that pharmaceutical/medicament that passes through the chamber 130 and the resin 135 therein can be administered to an individual. Those of skill in the art will appreciate that the needle 150 utilized with the filtering device 100 of the present disclosure can be of any suitable gauge and construction. The needle 150 of the filtering device 100 can be permanently affixed to the filtering device 100 at or near outlet 120, or may be removably attached to the device at the same location(s).

The inlet of 110 of the filtering device 100 is adapted to receive a pharmaceutical or medicament therein. Conventional pharmaceuticals and medicaments often contain preservatives, excipients and/or stabilizers which may have deleterious effects when introduced into the body of a patient receiving the pharmaceutical or medicament.

In certain configurations, the preservative may be a phenol or derivative thereof, such as m-cresol. As used herein, a phenol or phenolic compound means a composition that contains at least one phenol group. A phenol group is an aromatic hydrocarbon having a hydroxyl group bonded thereto ($C_6H_5O$). As used herein, a derivative of a phenol or phenolic compound means a compound having a phenol group that is substituted. For example, and without limitation, a phenolic derivative can be m-cresol, which is a phenol compound with a methyl substitution ($C_1H_5O$). Phenols/phenolic compounds and their derivatives are frequently used in commercial insulin preparations, and the present invention is suitable for the removal of such preservatives/excipients/stabilizers from commercial insulin preparations, such as HUMALOG® (insulin lispro) (Eli Lilly and Company, Indianapolis, Ind.), APIDRA® (insulin glulisine) (Sanofi S. A., Paris, France), and NOVOLOG® (insulin aspart) (Novo Nordisk A/S, Bagsvaerd, Denmark). These commercial preparations are merely exemplary, and those of skill in the art will appreciate that the present devices, systems, and methods can be utilized with any insulin preparation, commercial or otherwise, that contains preservatives, excipients, surfactants (ionic and non-ionic), and/or stabilizers. In embodiments, preservatives, excipients, surfactants, and stabilizers include benzyl alcohol, chlorobutanol, methylparaben, propylparaben, phenoxyethanol, and thimerosal.

The resin 135 disposed within the chamber 130 can be any suitable resin for the removal of preservatives, excipients, and stabilizers from a pharmaceutical or medicament, with the proviso that the resin is not a zeolite-based resin. Because of the increased force needed to pass solutions over/through filters based on zeolites, or other materials that filter based on size-exclusion, resins including such materials are not preferred and are not considered to be within the scope of the present disclosure. In embodiments, the resin selectively removes or filters a preservative, excipient, and/or stabilizer based on polarity or ionic interactions.

The resin 135 utilized in the filtering device 100 of the present disclosure can, in certain configurations, include a nonpolar compound. As used herein, the term nonpolar means that the component(s) of the resin do not include any permanently dipolar molecules. In certain configurations, the resin 135 includes or is a polystyrene. As used herein, the term polystyrene means an aromatic polymer of styrene monomers. As used herein, the term styrene means an aromatic hydrocarbon benzene derivative having the general formula $C_6H_5CH=CH_2$. Suitable polystyrene resins are commercially available from, for example and without limitation, Dow Chemical Co. (AMBERSORB™ 560, DOWEX™ OPTIPORE™ L493, DOWEX™ OPTIPORE™ SD-2, DOWEX™ XUS 43578, and DOWEX™ XUS 43600), Thermo Fisher Scientific (HiPPR) and Bio-Rad Laboratories, Inc. (Chelex®, Bio-Beads® SM2). In particularly preferred configurations, the resin is polystyrene-divinyl-benzene beads, such as Bio-Beads®

SM2 manufactured by Bio-Rad Laboratories, Inc. (Hercules, Calif.). Such beads may preferably have a pore diameter of less than about 100 angstroms (Å), for example, and without limitation, less than about 100, 95, 90, 85, 80, 75, 70, 65, 60, 55, 50, 45, or 40 Å. Those of skill in the art will appreciate that slight variations in pore size fall within the scope and spirit of the invention, depending on the pharmaceutical/medicament used and the preservatives/excipients/stabilizers included therewith. Without wishing to be bound thereby, a theory regarding the efficacy of these products is that polystyrene-containing resins, such as Bio-Beads® SM2, function in removing preservatives, excipients, and/or stabilizers from pharmaceutical preparations through hydrophobic interactions with such additives. To this end, the hydrophobicity of the resin materials is a consideration; however, pore size, surface area, and the difference in hydrophobicity of the surface as compared to the interior are also considerations.

However, for example in the case of insulin, the use of nonpolar resins that remove preservatives, excipients, and/or stabilizers through hydrophobic interactions, the pharmaceutical/medicament itself is also subject to removal from the composition ultimately administered to the patient. While some change in insulin concentration from the preparation can be considered acceptable, the preparation must have 95.0%-105.0% of the potency stated on the label, to comply with applicable requirements expressed in United States Pharmacopeia (USP), such as the USP Monograph for Insulins (Rev. Feb. 1, 2013). Accordingly, the length of time for which the pharmaceutical/medicament-containing solution is exposed to the resin is a factor, as will be discussed below.

In another configuration, the resin 135 of the filtering devices, systems, and methods of the present disclosure includes or is a carbonaceous material. As used herein, the term carbonaceous means rich in carbon, and can include activated carbon materials. In certain configurations, the carbonaceous material is AMBERSORB™ 560 manufactured by Dow Chemical Co. (Midland, Mich.), which is a polymeric material suitable for removing small organic molecules from aqueous solutions.

In addition to the above-identified resins, it is within the scope of the present disclosure to include other potentially useful additives in the chamber, to further filter or alter the pharmaceutical/medicament. For example, and without limitation, additives such as chelators/chelating agents can be included in the chamber, and/or resins that also include chelating capability can be utilized, and/or resins may be functionalized to include a chelating agent thereon. As used herein, the term chelator/chelating agent means a compound or composition, capable of forming one or more bonds with a metal ion. Such agents may be advantageous to include in the chamber and/or resin of the present disclosure, to, for example in the case of insulin, drive the disassociation of the hexameric form of insulin, to provide a greater percentage of insulin monomer. Suitable chelators will be known to those of skill in the art and will differ based on pharmaceutical preparation/medicament, each of which may have different metal ions included therewith. For example, and without limitation, in the case of insulin, an effective chelator/chelating agent will be one that chelates zinc ions ($Zn+^2$), often included in commercial insulin preparations. For example, and without limitation, suitable chelators can be ethylenediaminetetraacetic acid (EDTA). Suitable resins that include chelating functionality include DOWEX™ XUS 43578 (Dow Chemical Co., Midland, Mich.) and Chelex® resins (Bio-Rad Laboratories, Inc., Hercules, Calif.) Suitable chelators can be included in any level known to those of skill in the art to provide suitable removal of metal ions from a pharmaceutical preparation/medicament, and include, for example and without limitation, dipicolinic acid derivatives, pyridine derivatives such as derivatives of dipyridylamine (e.g., dipicolylamine), diethylenetriamine, ethylene glycol-bis(-aminoethyl ether)-N,N,N',N'-tetraacetic acid), phosphates, bisphosphates, and thiols.

Figure 4:
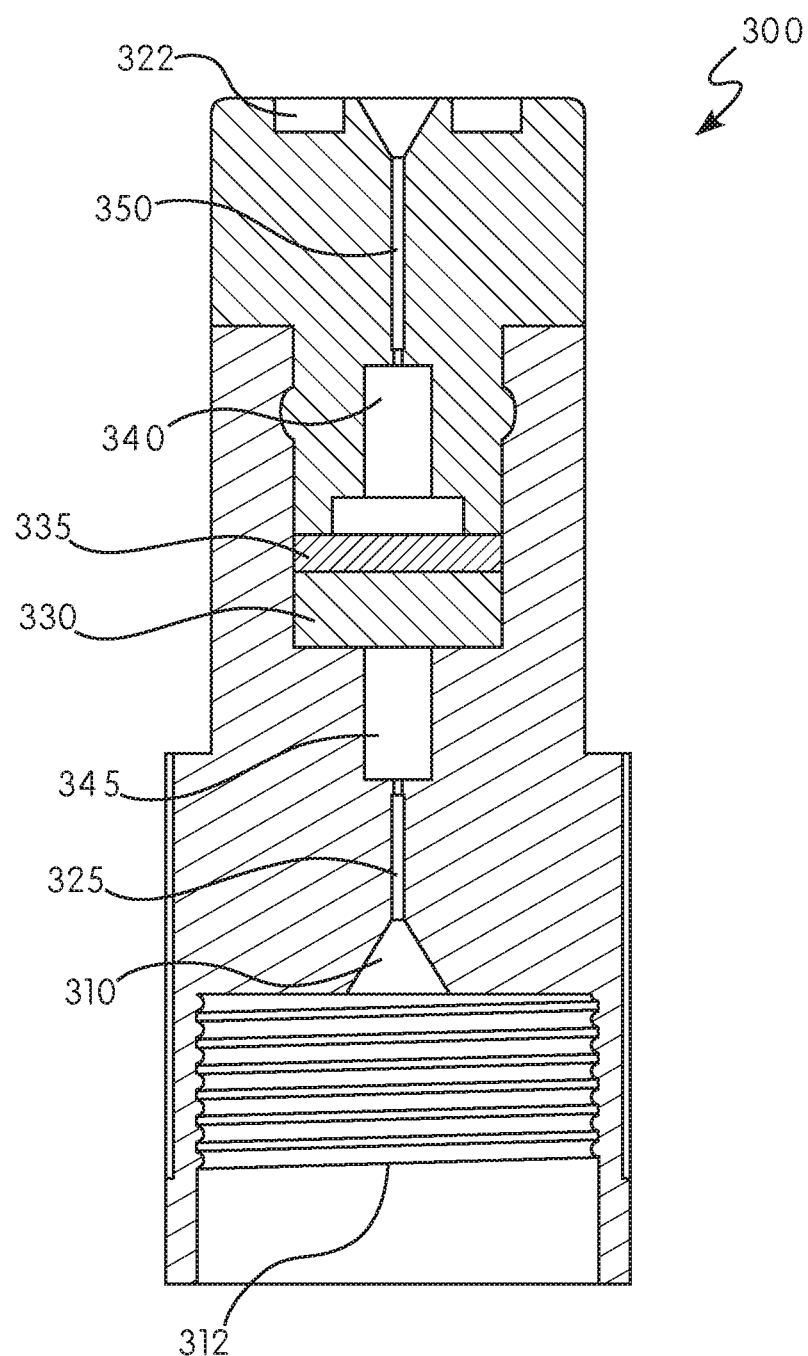
FIG. 4 is a schematic and cross-sectional representation (taken along line B-B) of a filtering device in accordance with an embodiment of the present invention.

With reference to FIG. 2, in embodiments, a device as described herein can include a second filter 145. In certain configurations, the filters 140, 145 can be arranged or configured such that they lie in the fluid flow channel 125 on either side of the chamber 130. That is, the filters 140, 145 can be arranged so that the resin is confined to the chamber 130 and portions the fluid flow channel 125 immediately adjacent thereto. Such an arrangement is useful to prevent withdrawal of resin 135 out of the chamber 130 and into a larger reservoir of the pharmaceutical, in configurations where the filtering device is provided as a unitary structure with an infusion or injection device. When the filtering device 100 is provided with any injection/infusion device that allows for withdrawal (via a plunger rod, reversal of pump flow, or vacuum) of pharmaceutical/medicament back into a reservoir or cartridge, the possibility exists that materials in the chamber 130 would likewise be withdrawn into the reservoir or cartridge. An arrangement of filters such as in FIG. 4 is important in view of the hydrophobic interaction of the resin and the pharmaceutical/medicament, for example insulin, as any transfer of resin 135 from the filtering device 100 to, for example, the reservoir or cartridge of an infusion/injection device, could reduce the efficacy of that composition. In certain configurations, at least one of the filters 140, 145 has an average pore size of between about 15 μm and about 45 μm, though those of skill in the art will appreciate that filters, including pore size, can be selected based on pharmaceutical/medicament to be administered and the particular resin 135 employed in the filtering device 100.

With reference to FIGS. 1 and 2, although the figures show a particular shape of both the filtering device 100 and chamber 130, those of skill in the art will appreciate that the body of the filtering device 100 may assume any useful shape or configuration, so long as pharmaceutical/medicament can come into contact with the resin 135 within the chamber 130. In addition, while chamber 130 is shown as being in the fluid flow channel 125, those of skill in the art will appreciate that the chamber 130 may surround a portion of the fluid flow channel 125, which may have pores therein for allowing flow of pharmaceutical/medicament from the fluid flow channel 125 to the chamber holding the resin 135, and flow from the chamber 130 back to the fluid flow channel 125 for continuing flow through filter 140 and to outlet 120. Those of skill in the art will appreciate that various configurations can be utilized, so long as the pharmaceutical/medicament comes into contact with the resin 135.

Figure 3:
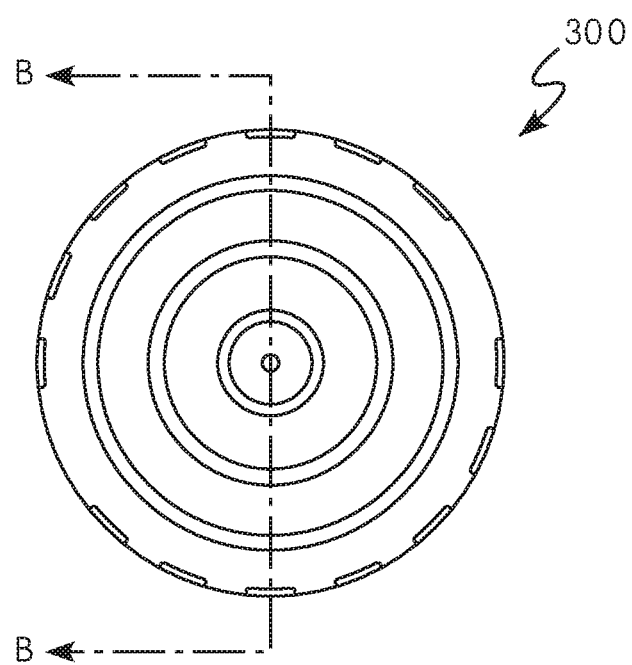
FIG. 3 is a schematic and cross-sectional representation (taken along line B-B) of a filtering device in accordance with an embodiment of the present invention.

With reference to FIGS. 3-4, shown is another embodiment of a filtering device, including a cross-sectional view along line B-B. Similar to the device shown in FIGS. 1 and 2, the device according to further embodiments includes a needle 350, an inlet 310 and an outlet 320, and a fluid flow channel 325 extending between the inlet 310 and the outlet 320. The fluid flow channel 325 is in fluid communication with outlet 320, at least one chamber 330 disposed within the body of the filtering device 300, and inlet 310. The chamber 330 includes a resin 335 therein, the resin provided for the filtering or removal of preservatives, excipients, or stabilizers included in a pharmaceutical or medicament. The filtering device 300 further includes at least one filter 340 disposed in the fluid flow channel 325 between the chamber 330 holding resin 335 and the outlet 320. In the illustrated embodiment of FIG. 3, connection 312 is a threaded connection for attachment to, for example, an autoinjector or pen injector.

With reference to FIG. 4, shown is a further embodiment with a threaded connection 322. Filtering device 100, 300, as illustrated in FIGS. 1-4, can be formed of any suitable material known to those of skill in the art. In certain configurations, the filtering device 100 has a body made of, for example, polypropylene, polystyrene, or polycarbonate. However, those of ordinary skill will appreciate that these materials are merely exemplary, and that any suitable polymers can be utilized. The filtering device 100 can be manufactured as a single molded device, or in two or more segments, allowing for alterations in chamber 130 size.

Filtering device 100, 300 illustrated in FIGS. 1-4 is suitable for use with syringes, autoinjectors, and pen injectors, whether reusable or disposable, as will be discussed below.

Figure 5:
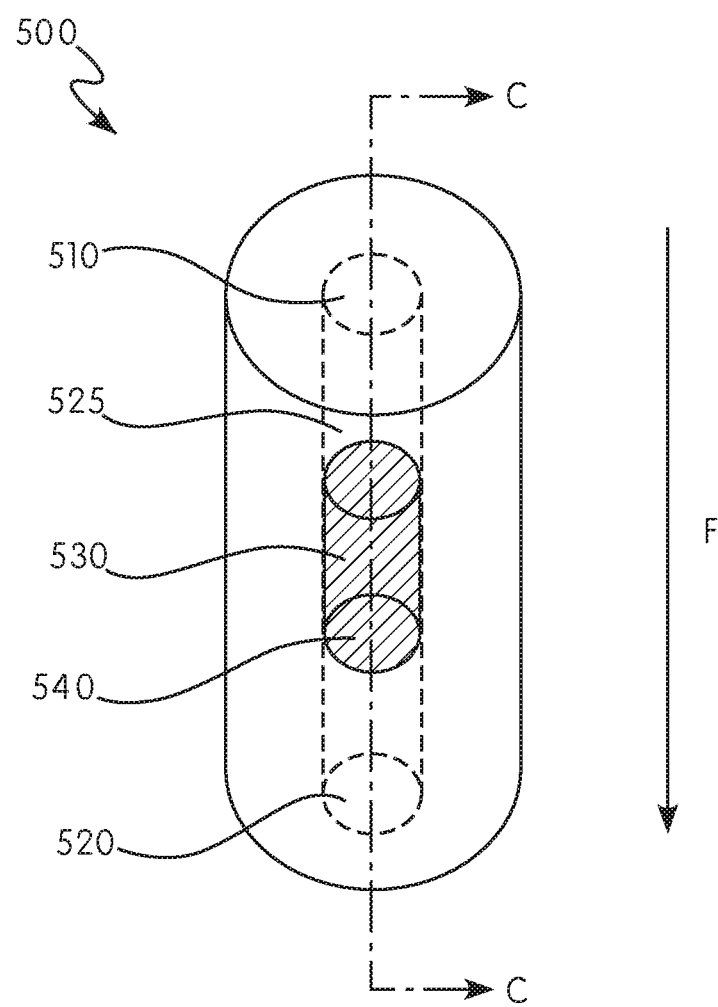
FIG. 5 is a schematic representation of a filtering device in accordance with an embodiment of the present invention.
Figure 6:
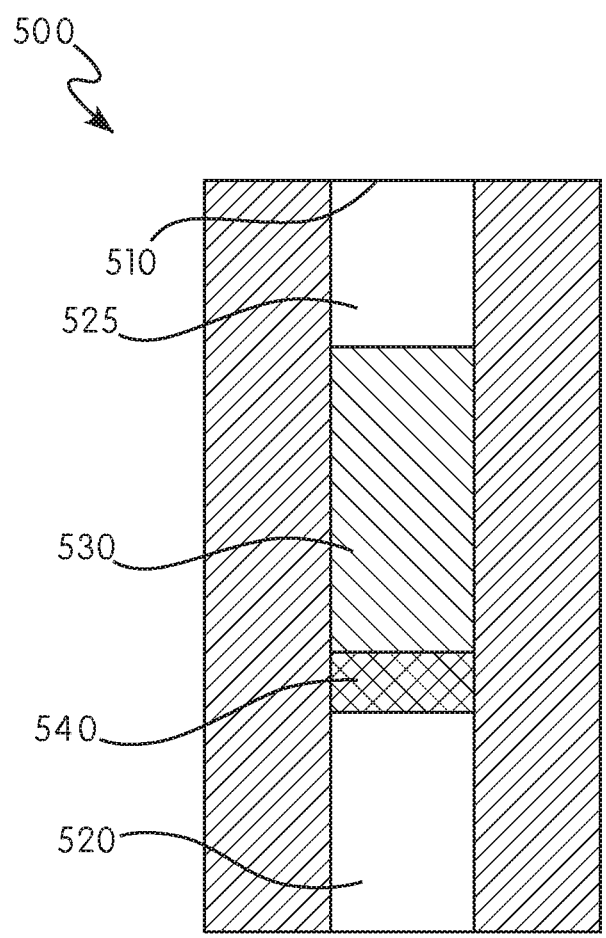
FIG. 6 is a cross-sectional view of a filtering device in accordance with an embodiment of the present invention taken along line C-C of FIG. 5.

In addition to syringes, autoinjectors, and pen injectors, the filtering device of the present disclosure can also be adapted for use with infusion systems, such as pumps and patch infusion systems. Those of skill will appreciate that the filter device of the present disclosure can be utilized in a variety of commercial pumps/patch infusion systems, such as, for example and without limitation, the LIBERTAS™ wearable injector, manufactured by Becton, Dickinson and Company (Franklin Lakes, N.J.) and the FlowSmart™ Infusion Set, also manufactured by Becton, Dickinson and Company. The filtering device of the present disclosure can be included in such systems by in-line provision (FIGS. 5-8) or through an attachment onto existing pump/patch infusion systems (FIG. 9). With reference to FIGS. 5 and 6, illustrated is a configuration of the filtering device 500. The filtering device 500 includes an inlet 510 and an outlet 520, with the body configured to define a fluid flow channel 525 (with flow direction indicated as F in FIG. 5) between the inlet 510 and the outlet 520. The fluid flow channel 525 is in fluid communication with at least one chamber 530 disposed within the body of the filtering device 500. The chamber 530 includes a resin (not shown) therein, the resin provided for the filtering or removal of preservatives, excipients, or stabilizers included in a pharmaceutical or medicament. The filtering device 500 further includes at least one filter 540 disposed in the fluid flow channel 525. While FIG. 5 shows a particular arrangement of both the filtering device 500 and chamber 530, those of skill in the art will appreciate that the body of the filtering device 500 may assume any useful shape or configuration, so long as pharmaceutical/medicament can come into contact with the resin within the chamber 530 and so long as the filtering device can be utilized in-line with an pump/patch infusion system. As above, the present disclosure also contemplates that the chamber 530 can surround a portion of fluid flow channel 525, and that pharmaceutical/medicament can flow from the channel 525 to the resin in the chamber 530 through pores in the channel 525, and then back to the channel 525 for flow through filter 540 and through outlet 520. Those of skill in the art will appreciate that various configurations can be utilized, so long as the pharmaceutical/medicament comes into contact with the resin 535.

Figure 7:
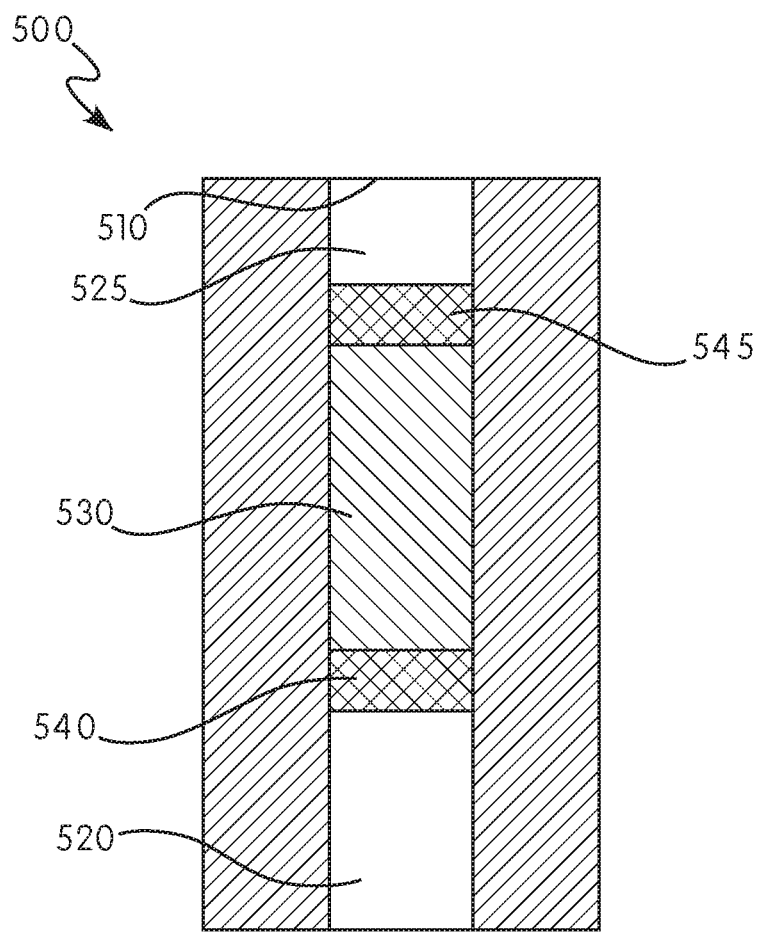
FIG. 7 is a cross-sectional view of a filtering device in accordance with an embodiment of the present invention taken along line C-C of FIG. 5.

In accordance with a further embodiment of the present disclosure, and with reference to FIGS. 6 and 7, which show a cross-section view of the exemplary embodiment of the filtering device of FIG. 5, along line C-C of FIG. 5, in certain configurations the filtering device 560 for use in a pump/patch infusion system can include a second filter 545 (FIG. 7). In certain configurations, such as shown in FIG. 7, the filters 540, 545 can be arranged or configured such that they lie in the fluid flow channel 525 on either side of the chamber 530. That is, the filters 540, 545 can be arranged so that the resin is confined to the chamber 530 and portions the fluid flow channel 525 immediately adjacent thereto. Such an arrangement is useful to prevent withdrawal of resin 535 out of the chamber 530 and into a larger reservoir of the pharmaceutical, in configurations where the filtering device is provided as a unitary structure with an infusion or injection device. Such an arrangement is important in view of the hydrophobic interaction of the resin and the pharmaceutical/medicament, for example insulin, as any transfer of resin 535 from the filtering device 500 to, for example, the reservoir of an infusion/injection device, could reduce the efficacy of that composition. In certain configurations, at least one of the filters 540, 545 has an average pore size of between about 15 µm and about 45 µm, though those of skill in the art will appreciate that filters, including pore size, can be selected based on pharmaceutical/medicament to be administered and the particular resin employed in the filtering device 500.

Figure 8:
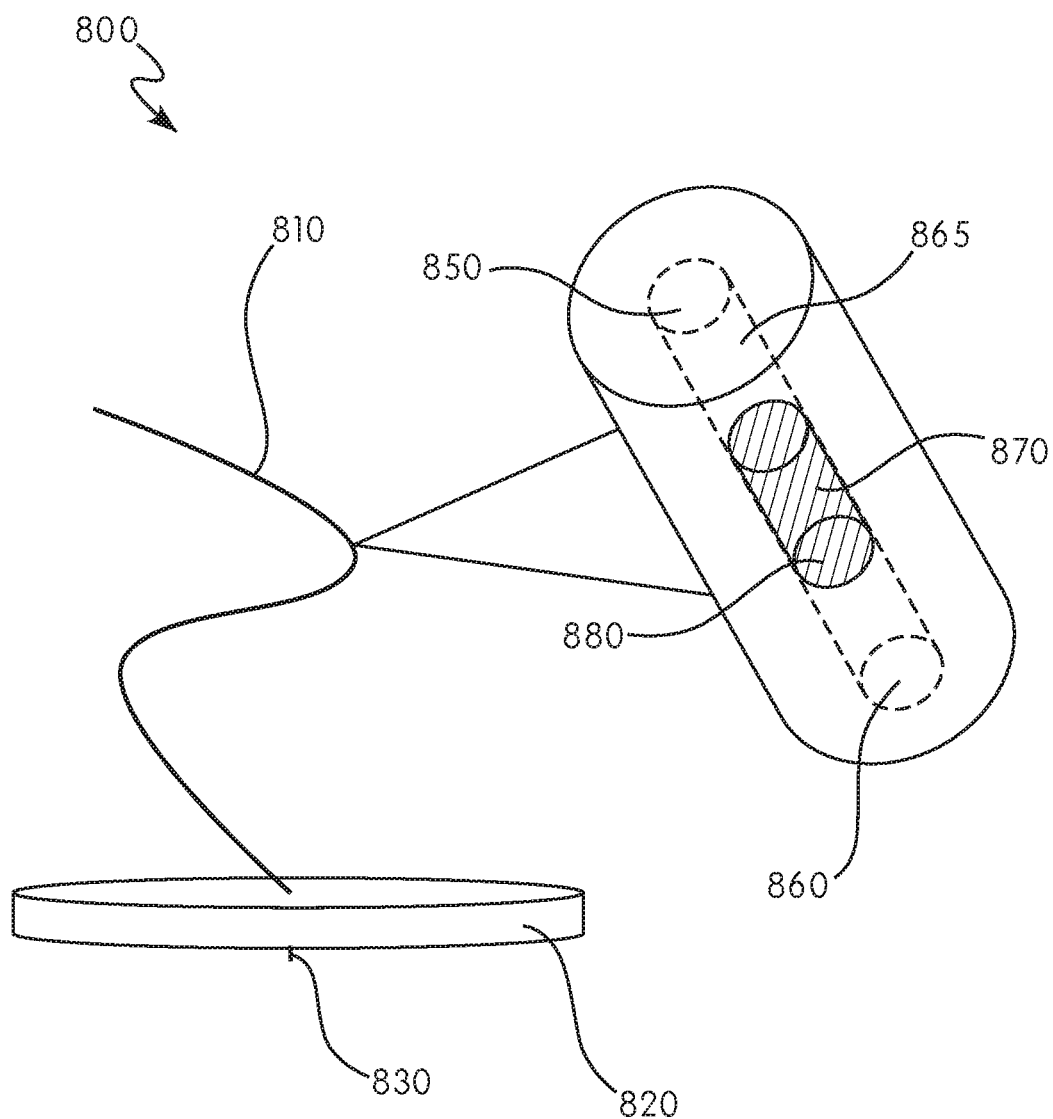
FIG. 8 is a schematic representation of a system including an injection device and a filtering device in accordance with an embodiment of the present invention.
Figure 9:
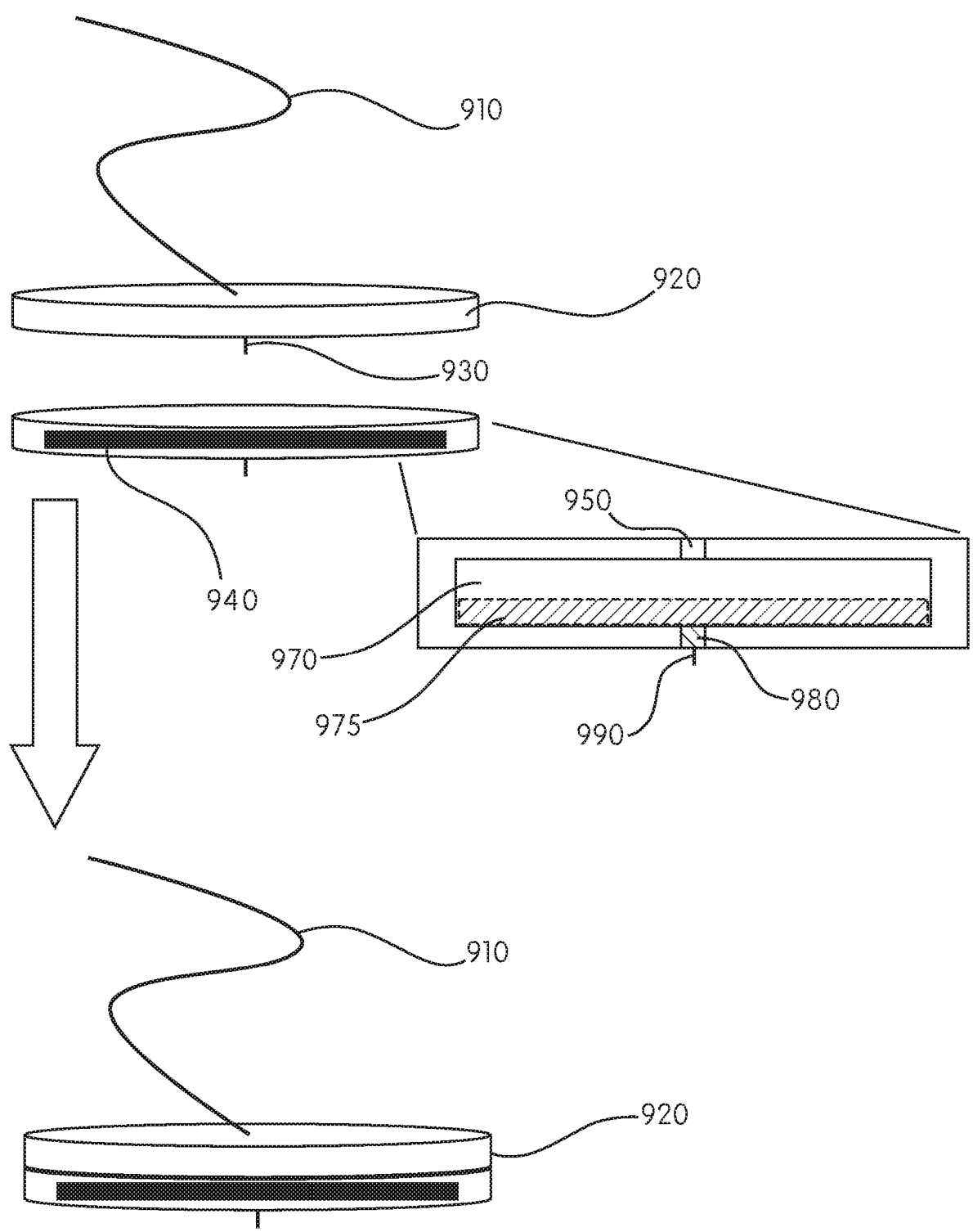
FIG. 9 is a schematic representation of a system including an injection device and a filtering device in accordance with an embodiment of the present invention.

FIG. 8 illustrates an exemplary pump/patch infusion system 800 including tubing 810 and skin attachment 820 including needle 830. While not shown, those of skill in the art will appreciate that the pump/patch infusion system as shown will include a cartridge or reservoir containing the pharmaceutical/medicament to be administered. In the configuration shown in FIG. 8, the filter device 840 is provided in-line, in the tubing 810. This filter may be permanently provided within the tubing 810, and such tubing 810 including the filter device 840 can be disposable or reusable for 1, 2, 3, 4, 5, 6, 7, 8, 9, 10, or more pharmaceutical/medicament administrations. Alternatively, in certain configurations, filter device 840 can be provided as a removable insert in tubing 810. That is, the filter device 840 can be disposable, and the tubing 810 may be reusable.

As shown in prior illustrations, filter device 840 includes an inlet 850 and an outlet 860, with the body configured to define a fluid flow channel 865 between the inlet 850 and the outlet 860. The fluid flow channel 865 is in fluid communication with at least one chamber 870 disposed within the body of the filtering device 840. The chamber 870 includes a resin 875 therein, the resin provided for the filtering or removal of preservatives, excipients, or stabilizers included in a pharmaceutical or medicament. The filtering device 840 further includes at least one filter 880 disposed in the fluid flow channel 865. While FIG. 8 shows a particular arrangement of both the filtering device 840 and chamber 870, those of skill in the art will appreciate that the body of the filtering device 840 may assume any useful shape or configuration, so long as pharmaceutical/medicament can come into contact with the resin 875 within the chamber 870 and so long as the filtering device can be utilized in-line with an pump/patch infusion system.

In certain other embodiments, rather than being provided in-line in the tubing of a pump/patch infusion system, the filtering device of the present disclosure can be provided as an add-on to be provided between the normal skin attachment/delivery interface of the pump/patch infusion system and the patient. That is, the filter can be configured to attach to the normal skin attachment/delivery interface of the pump/patch infusion system, through interaction with the needle on such systems. With reference to FIG. 9, illustrated is an exemplary pump/patch infusion system 900 including tubing 910 and skin attachment 920 including needle 930. While not shown, those of skill in the art will appreciate that the pump/patch infusion system as shown will include a cartridge or reservoir containing the pharmaceutical/medicament to be administered.

In the configuration shown in FIG. 9, the filtering device 940 includes inlet 950 and an outlet, with the body configured to define a fluid flow channel between the inlet 950 and the outlet 960. The fluid flow channel is in fluid communication with at least one chamber 970 disposed within the body of the filtering device 940. The chamber 970 includes a resin 975 therein, the resin provided for the filtering or removal of preservatives, excipients, or stabilizers included in a pharmaceutical or medicament. The filtering device 940 further includes at least one filter 980 disposed in the fluid flow channel 965. While FIG. 9 shows a particular arrangement of both the filtering device 940 and chamber 970, those of skill in the art will appreciate that the body of the filtering device 940 may assume any useful shape or configuration, so long as pharmaceutical/medicament can come into contact with the resin 975 within the chamber 970 and so long as the filtering device can be utilized as an attachment to a typical pump/patch infusion system. In certain configurations the filtering device 940 can include a needle 990, which may be permanently affixed or removably attached at or near outlet.

As described above, the filtering device illustrated in FIGS. 1-4 is suitable for use with syringes, autoinjectors, and pen injectors. Also included within the scope of the present disclosure is a system including an injection device, which device may be a syringe, an autoinjector, or a pen injector. The injection device includes a housing or body defining a chamber configured to or capable of holding a pharmaceutical or medicament, a displaceable plunger rod disposed at least partially within the housing, and an outlet in fluid communication with the chamber. The syringe, autoinjector, or pen injector may be any commercially available device, such as, for example and without limitation, a BD NEOPAK™ pre-filled syringe, a BD™ Reusable Pen, a VYSTRA™ disposable pen injector, or a PHYSIOJECT™ disposable autoinjector, each manufactured by Becton, Dickinson and Company (Franklin Lakes, N.J.).

The filtering device includes inlet and an outlet, with the body configured to define a fluid flow channel between the inlet and the outlet. The fluid flow channel is in fluid communication with at least one chamber disposed within the body of the filtering device. The chamber includes a resin therein, the resin provided for the filtering or removal of preservatives, excipients, or stabilizers included in a pharmaceutical or medicament. The filtering device further includes at least one filter disposed in the fluid flow channel. Those of skill in the art will appreciate that the body of the filtering device may assume any useful shape or configuration, so long as pharmaceutical/medicament can come into contact with the resin within the chamber and so long as the filtering device can be utilized as an attachment to a syringe, autoinjector, or pen injector.

In some configurations, the filtering device includes a needle. The needle can be permanently affixed to the filtering device, for example originating within the fluid flow channel. In other configurations, the needle can be disposed externally at or near outlet, so that pharmaceutical/medicament that passes through the chamber and the resin therein can be administered to an individual. Those of skill in the art will appreciate that the needle utilized with the filtering device of the present disclosure can be of any suitable gauge and construction. The needle of the filtering device can be permanently affixed to the filtering device at or near outlet, or may be removably attached to the device at the same location(s).

The filtering device can be permanently attached, whether to a disposable device, such as an autoinjector, or a reusable device, such as a pen injector. In certain configurations, the filtering device can be removably attached to either a disposable device or a reusable device.

Also provided in the present disclosure is a method of removing a preservative, excipient, or stabilizer from a pharmaceutical/medicament. The method is suitable for use with the devices and systems disclosed herein, and includes passing the pharmaceutical through a filtering device, such as, for example and without limitation, that illustrated in FIGS. 1-7, and the systems illustrated in FIGS. 8-10. The filtering device includes an inlet and an outlet, with the body configured to define a fluid flow channel between the inlet and the outlet. The fluid flow channel is in fluid communication with at least one chamber disposed within the body of the filtering device. The chamber includes a resin therein, the resin provided for the filtering or removal of preservatives, excipients, or stabilizers included in a pharmaceutical or medicament. The filtering device further includes at least one filter disposed in the fluid flow channel.

As described previously, the resin utilized in the filtering device of the present disclosure can, in certain configurations, include a nonpolar compound and, in certain configurations, the resin includes or is a polystyrene that can function in removing preservatives, excipients, and/or stabilizers from pharmaceutical preparations through hydrophobic interactions with such additives. However, as also described above, for example in the case of insulin, the use of nonpolar resins that remove preservatives, excipients, and/or stabilizers through hydrophobic interactions, the pharmaceutical/medicament itself is also subject to removal from the composition ultimately administered to the patient. Thus, the time for which the pharmaceutical/medicament is exposed to the resin is a factor. To this end, in certain configurations the pharmaceutical/medicament is exposed to the resin in the filtering device for less than 300 minutes, preferably less than 200 minutes, more preferably less than 100 minutes, and most preferably, less than 50 minutes. In a preferred configuration, the pharmaceutical/medicament is exposed to the resin for five minutes or less.

Figure 14:
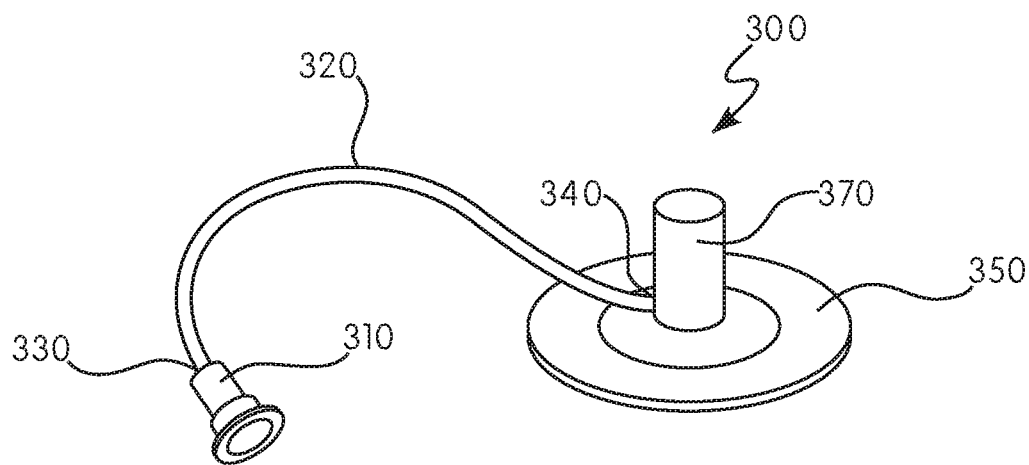
FIG. 14 is a schematic representation of an infusion set in accordance with an embodiment of the present invention.

With reference to FIG. 14, an anti-inflammatory, controlled release infusion set 300 (hereinafter referred to as "infusion set 300") is shown in accordance with one example. The infusion set 300 may be configured for use with infusion systems, such as pumps and patch infusion systems, configured for extended use (three days or longer) while connected to a patient. Those of skill will appreciate that the infusion set 300 of the present disclosure can be utilized in a variety of commercial pumps/patch infusion systems, such as, for example and without limitation, the LIBERTAS™ wearable injector, manufactured by Becton, Dickinson and Company (Franklin Lakes, N.J.). Although FIG. 14 shows a particular shape of the infusion set 300, those of skill in the art will appreciate that the infusion set 300 may assume any useful shape or configuration, so long as the infusion set 300 is configured for delivering a dose of the anti-inflammatory agent.

The infusion set 300 of the present disclosure can include the filter device, such as the filter device 840 discussed herein with reference to FIG. 8. The combined filtration/controlled release infusion set is configured to address device- and excipient-induced biocompatibility concerns to extend the wear time of the infusion set 300. In some examples, the wear time of the infusion set 300 may be seven (7) to ten (10) days.

With continued reference to FIG. 14, the infusion set 300 has a connector 310 configured for connecting to the infusion pump. While not shown, those of skill in the art will appreciate that the infusion pump generally includes a cartridge or reservoir containing the pharmaceutical/medicament to be administered. In some examples, the connector 310 may be a threaded connector, such as a luer-lock, configured for connecting to the infusion pump. Tubing 320 is connected at its proximal end 330 to the connector 310. The tubing 320 may be removably or non-removably connected to the connector 310 at its distal end 330. The tubing 320 is configured to allow the pharmaceutical/medicament to flow from the infusion pump to the patient through an internal lumen of the tubing 320. A proximal end 340 of the tubing 320 is connected to a dermal pad 350 that is configured for attaching to a patient's skin. In some examples, the dermal pad 350 has an adhesive that facilitates removable connection of the dermal pad 350 to the patient's skin.

The infusion set 300, as illustrated in FIG. 14, can be formed of any suitable material known to those of skill in the art. In certain configurations, at least a portion of the infusion set 300 may be made of, for example, polypropylene, polystyrene, or polycarbonate. However, those of ordinary skill will appreciate that these materials are merely exemplary, and that any suitable polymers can be utilized. The infusion set 300 can be manufactured as a single molded device, a co-molded device, or a device having a plurality of separate components that are removably or non-removably connected together.

Figure 15:
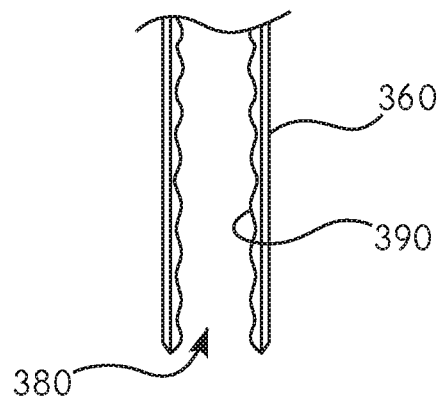
FIG. 15 is a cross-sectional view of a needle for use with the infusion set of FIG. 14.

The proximal end 340 of the tubing 320 is in fluid communication with a needle 360. Those of skill in the art will appreciate that the needle 360 utilized with the infusion set 300 of the present disclosure can be formed of any suitable gauge and construction. The needle 360 of the infusion set 300 can be permanently affixed to the proximal end 340 of the tubing 320, or may be removably attached to the infusion set 300 at the same location. In other configurations, the needle 360 can be disposed externally of the tubing 320 and be in fluid communication with the tubing 320, such as by way of a manifold 370. The needle 360, as illustrated in FIGS. 14-15, can be formed of any suitable material known to those of skill in the art. In certain configurations, the needle 360 may be made of, for example, metal, such as a stainless steel. However, those of ordinary skill will appreciate that this material is merely exemplary, and that any suitable materials can be utilized. The needle 360 has a central lumen 380 extending in a direction along a longitudinal axis of the needle 360. Optionally, one or more side apertures (not shown) may extend through a sidewall of the needle 360 in a direction that is perpendicular or angled relative to a direction of the central lumen 380.

With continued reference to FIG. 14, the infusion set 300 has an anti-inflammatory agent associated therewith for controlled release into the patient's body. The infusion set 300 may be configured to deliver a dose of the anti-inflammatory agent in a therapeutically-effective amount at a predetermined delivery rate. For example, the anti-inflammatory agent may be any type of drug, chemical, biological, or biochemical substance that, when delivered in a therapeutically-effective amount, achieves a desired anti-inflammatory effect during a prolonged use of the infusion set 300. In some examples, the anti-inflammatory agent may be a steroidal or non-steroidal anti-inflammatory agent. In various examples, the anti-inflammatory agent may be configured to ameliorate the inflammatory effects of excipient infusion through decreased proinflammatory cytokine release.

Controlled release of the anti-inflammatory agent may be effected by coating at least a portion of the needle 360 with the anti-inflammatory agent, loading the adhesive of the dermal pad 350 with the anti-inflammatory agent, or a combination thereof.

Figure 16:
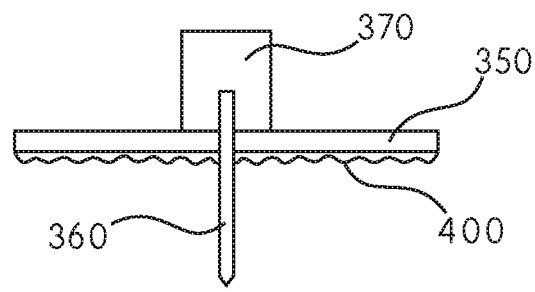
FIG. 16 is a cross-sectional view of a dermal pad for use with the infusion set of FIG. 14.

With reference to FIGS. 15-16, an enlarged portion of the needle 360 configured for use with the infusion set 300 is shown. A coating 390 having an anti-inflammatory agent may be formed on an interior surface 400 of the central channel 380 of the needle 360. The coating 390 may be formed along at least a portion of the interior surface 400 of the needle 360 between a proximal end and a distal end of the needle 360. In some examples, the coating 390 may be formed on at least a portion of an exterior surface of the needle 360. In further examples, the coating 390 may be formed on at least a portion of the interior surface 400 and at least a portion of the exterior surface of the needle 360. The coating 390 may be formed on the needle 360, for example, by freeze-drying a composition comprising the anti-inflammatory agent. Those of ordinary skill will appreciate that various other methods may be used to form the coating 390 on at least a portion of the needle 360. The coating 390 is configured to be eluted by the pharmaceutical/medicament that is infused through the needle 360. In some examples, the coating may be configured to be eluted by the patient's blood when the needle 360 is inserted into the patient's body. In further examples, the coating 390 may be configured to be eluted by the pharmaceutical/medicament that is infused through the needle 360 and the patient's blood when the needle 360 is inserted into the patient's body. In some examples, a release rate of the anti-inflammatory agent may be constant over the wear time of the infusion set 300. In other examples, the release rate of the anti-inflammatory agent 300 may be variable over the wear time of the infusion set, such that the rate increases or decreases over the wear time of the infusion set 300.

With reference to FIG. 16, a side cross sectional view of the dermal pad 350 is shown. An adhesive having an anti-inflammatory agent may be formed on a bottom surface of the dermal pad 350. The adhesive may be formed along at least a portion of the bottom surface of the dermal pad 350. Those of ordinary skill will appreciate that various other methods may be used to form the adhesive with the anti-inflammatory agent. The adhesive is configured to be released into the patient's body through physical contact with the patient's skin. In some examples, a release rate of the anti-inflammatory agent may be constant over the wear time of the infusion set 300. In other examples, the release rate of the anti-inflammatory agent may be variable over the wear time of the infusion set 300, such that the rate increases or decreases over the wear time of the infusion set 300.

EXAMPLES

Evaluation of the Efficacy of Resins in Removing Phenolic Preservatives from a Commercial Diluent Six commercially-available resins were identified for testing efficacy of removal of phenolic preservatives/excipients from the diluent utilized by Eli Lilly and Company in its commercial insulin preparation HUMALOG®. Specifically, the resins that were utilized were the following:

| | DOWEX™ XUS 43578 | AMBERSORB™ 560 | DOWEX™ OPTIPORE™ L493 | DOWEXM™ OPTIPORE™ SD-2 | Chelex® | Bio-Beads® SM2 |
|---|---|---|---|---|---|---|
| Vendor | Dow | Dow | Dow | Dow | Bio-Rad | Bio-Rad |
| Polymer | Styrene/DVB | Styrene | Styrene | Styrene/DVB | Styrene/DVB | Styrene/DVB |
| Water Retention Capacity (%) | 40-60 | n/a | 50-65 | 50-62 | n/a | 35-55 |
| Particle Size Distribution (μm) | 297-841 | 297-841 | 297-841 | n/a | n/a | n/a |
| Functionality | Dipicolylamine | n/a | n/a | Tertiaryamine | Iminodiacetate | none |

Figure 10:
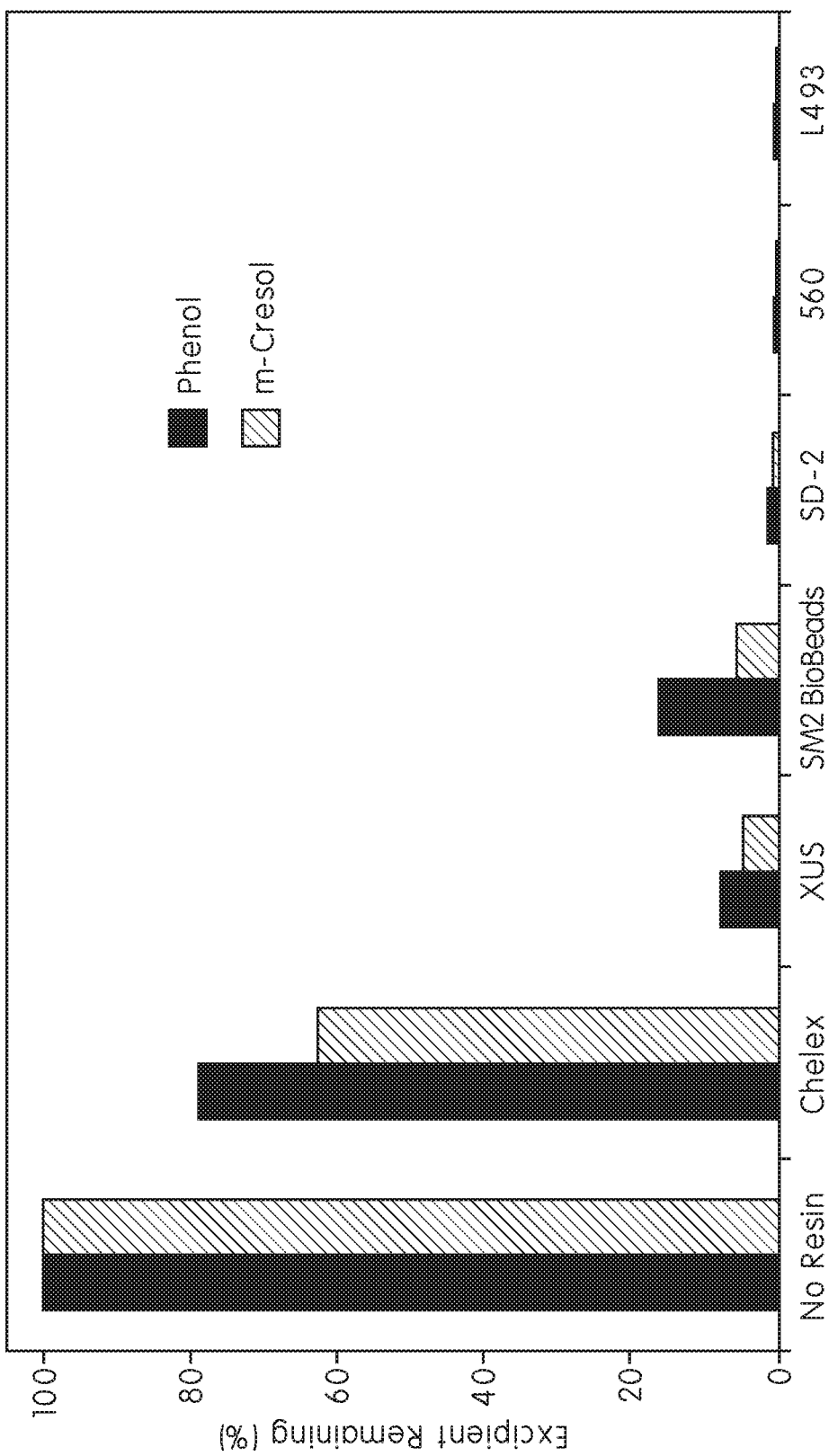
FIG. 10 shows efficacy of a number of resins for removing preservatives/excipients from a commercial diluent, in accordance with an embodiment of the present invention.

For this initial proof-of-concept study, 1 mL of diluent (1.6 mg m-cresol, 0.65 mg phenol) was incubated with 200 mg of each of the above-identified resins, together with a negative control (no resin) for 30 minutes. Levels of excipients remaining after incubation were determined using high-performance liquid chromatography. Detection occurred at 254 nm using a Zorbax 300SB-C18 column with 2 ml/min flow. The liquid was a gradient water with 5% acetonitrile (CAN) and goes to 95% CAN. The run time was 12 min with a 3 min equilibration. FIG. 10 shows the results of the incubation. With no resin utilized, 100% of the excipients remained in the diluent after 30 minutes. The resins removed, at a minimum, 20% of the excipients (Chelex®- 20% of phenol and 40% of m-cresol), and the remaining resins removed at least 80% of the excipients. DOWEX™ OPTIPORE™ SD-2, DOWEX™ OPTIPORE™ L493, and AMBERSORB™ 560 (Dow Chemical Co., Midland, Mich.) removed the greatest percentage of excipients. Bio-Beads® SM2 (Bio-Rad Laboratories, Inc., Hercules, Calif.) and XUS 43578 (Dow Chemical Co., Midland, Mich.) removed a lesser percentage of excipient, but still removed at least 80% of excipients. Bio-Rad Bio-Beads® SM2 removed 80% of phenol and >90% of m-cresol, and XUS 43578 removed >90% of both excipients. Thus, the results support the use of various resins for the removal of preservatives/excipients from pharmaceutical preparations.

Time-Course of Excipient Removal from a Commercial Diluent Using Resins

Following up on the above results, the next step was to determine the time course of excipient removal. Two resins were selected for further investigation, Bio-Beads® SM2 and Ambersorb 560. As above, 1 mL of diluent (Eli-Lilly and Company) was incubated in 200 mg of each resin. At t=0, 5, 10, 15, 20, 25, and 30 minutes, 10 μl aliquots of diluent were removed and analyzed for excipient levels as described above.

Figure 11:
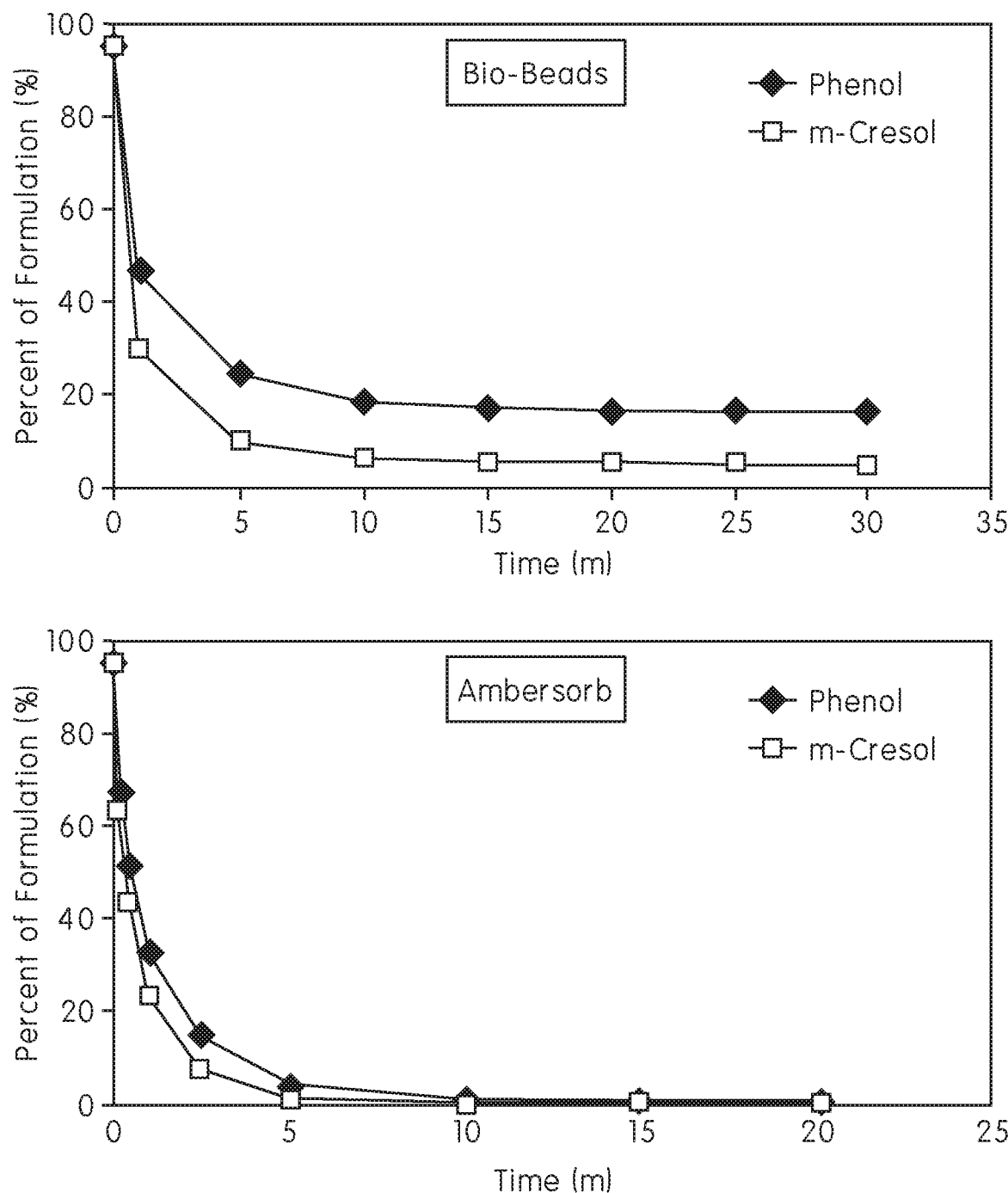
FIG. 11 shows a time-course of preservative/excipient removal by resins, in accordance with an embodiment of the present invention.

FIG. 11 shows the time-course for excipient removal for each resin (top panel—Bio-Beads® SM2; bottom panel—Ambersorb 560). As seen in the figure, each resin removed 80% of the excipients after 5 minutes, with Ambersorb effectively removing 100% of excipients after 20 minutes. The difference in results may relate to the different hydrophobicity levels between AMBERSORB™ 560 (higher) and Bio-Beads® SM2 (lower). These results support the use of various resins for the rapid removal of preservatives/excipients from pharmaceutical preparations/medicaments.

Evaluation of the Efficacy of Resins in Removing Phenolic Preservatives from Commercial Insulin Preparations In order to further investigate the efficacy of resins for use in the removal of preservatives/excipients, two resins were selected for evaluation of efficacy of removal from commercial insulin preparations, HUMALOG® (insulin lispro) (Eli Lilly and Company, Indianapolis, Ind.) and APIDRA® (insulin glulisine) (Sanofi S. A., Paris, France). For this experiment, 0.5 mL of lispro or glulisine was incubated with 100 mg of resin (Bio-Beads® SM2 or AMBERSORB™ 560). As with the above time-course experiment, 10 μL aliquots of the solution were removed from the incubation at certain time points (t=5, 10, 30, 60, 120, and 360 minutes), and were analyzed for excipient levels as described above.

HPLC Protocol

HPLC with UV detection, 254 nm wavelength, was utilized to detect insulin and excipient levels. Buffer A=5% (v/v) acetonitrile in water with 0.1% (v/v) TFA; Buffer B=5% (v/v) water in acetonitrile with 0.1% (v/v) TFA. The time table for the HPLC went as follows:

| Time (min) | % Buffer B | Flow Rate (ml/min) | Temp (° C.) |
|---|---|---|---|
| 0 | 20 | 2 | 50 |
| 6.2 | 35 | 2 | 50 |
| 6.7 | 90 | 2 | 50 |
| 8.4 | 90 | 2 | 50 |
| 9 | 20 | 2 | 50 |
| 12 | 20 | 2 | 50 |

Figure 12A:
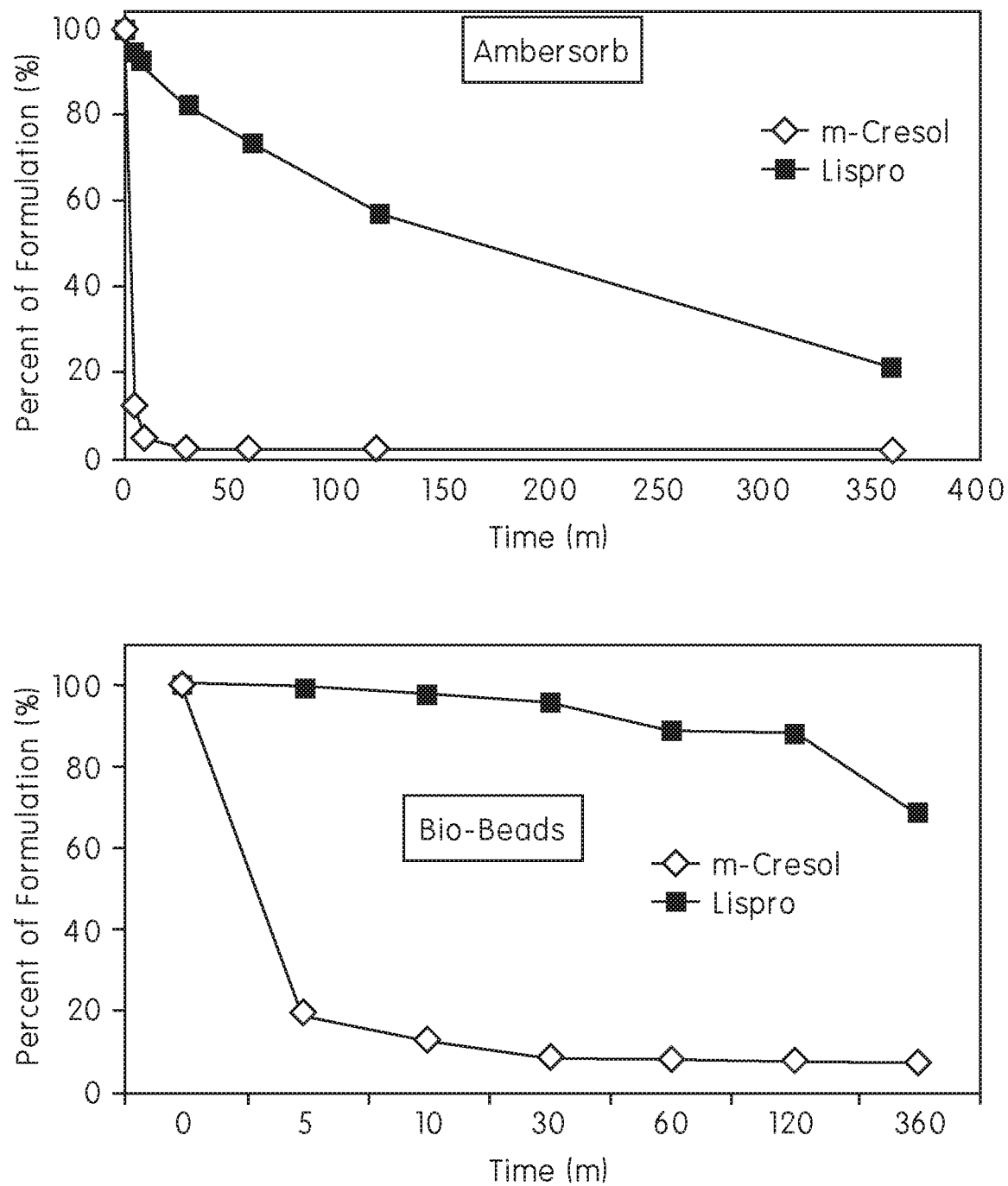
FIG. 12A-12B shows efficacy of preservative/excipient removal and maintenance of insulin levels of resins in commercial insulin preparations in accordance with an embodiment of the present invention.
Figure 12B:
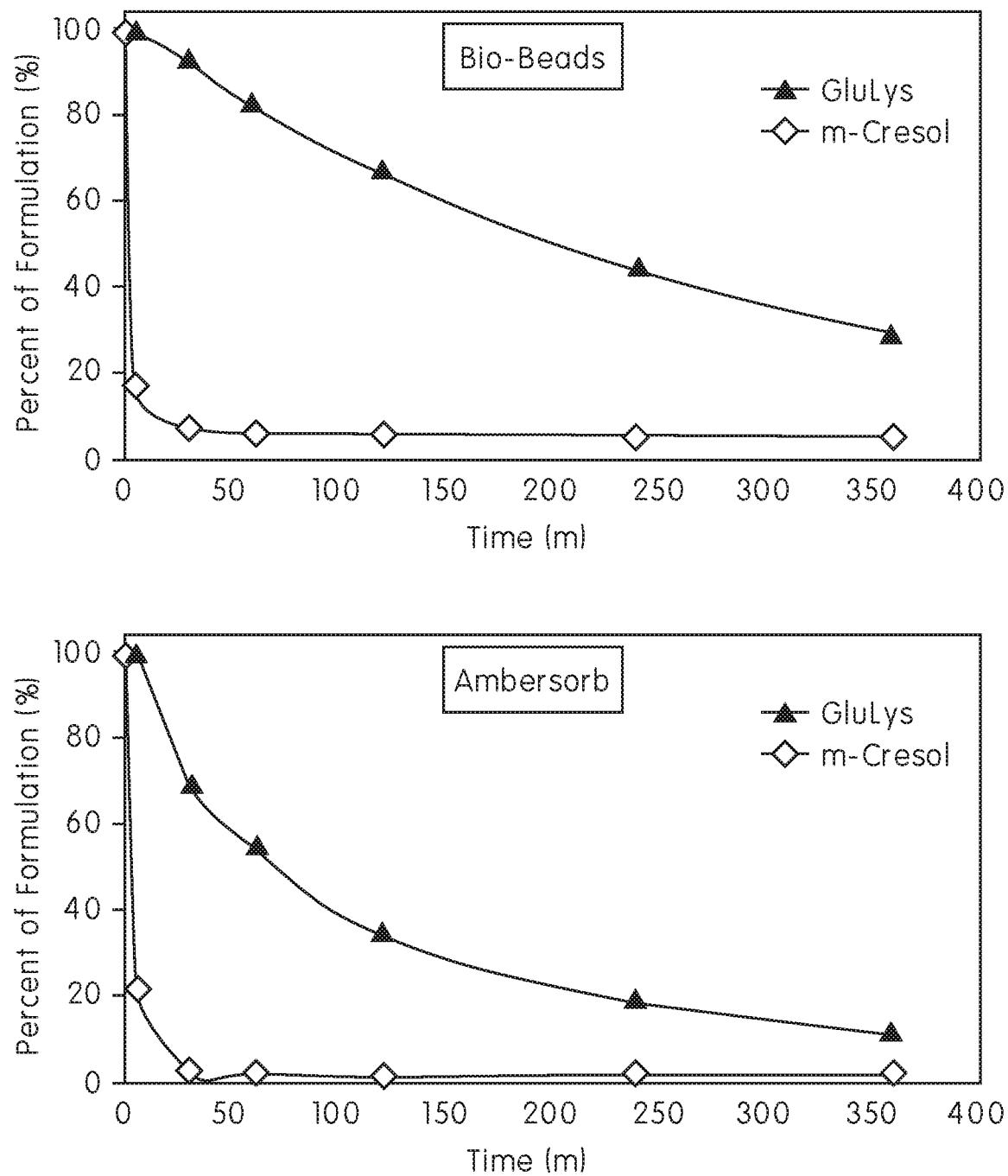

FIG. 12A-12B shows the time-course of excipient and insulin removal from the preparation. As can be seen from the figure, Bio-Beads® SM2 (lower panel) were more effective at removing excipients (m-cresol) while maintaining insulin levels. In the lispro experiment, after 120 minutes of incubation with Bio-Beads® SM2, almost 90% of insulin still remained in the solution, while less than 10% of the excipient was still present (FIG. 12A). In contrast, in the Ambersorb incubation (top panel), after 120 minutes only 60% of insulin still remained in the solution (FIG. 12A). In the glulisine experiment, after 120 minutes over 60% of insulin remained after incubation with Bio-Beads® SM2 (top panel), while again less than 10% of excipient was still present (FIG. 12B). Again, in contrast, in the Ambersorb incubation (lower panel) after 120 minutes less than 40% of insulin still remained in the solution, while less than 10% of excipient was still present (FIG. 12B). These results show that incubation with certain resins can effectively remove preservatives/excipients from pharmaceutical preparations, while leaving a sufficient amount of the pharmaceutical itself present in the preparation.

Efficacy of a Resin in Removing Preservatives from a Commercial Insulin Preparation Over Time Based on the above results, the efficacy of a single resin was evaluated over repeated exposure to a commercial insulin preparation, to see if there is a saturation level beyond which the resin cannot continue to remove preservatives/excipients.

In this study, repeated aliquots of a commercial insulin preparation, HUMALOG® (insulin lispro) (Eli Lilly and Company, Indianapolis, Ind.), were incubated with a single aliquot of 100 mg of AMBERSORB™ 560 resin. Aliquots were removed from the incubation every five minutes and analyzed (as described above).

Figure 13:
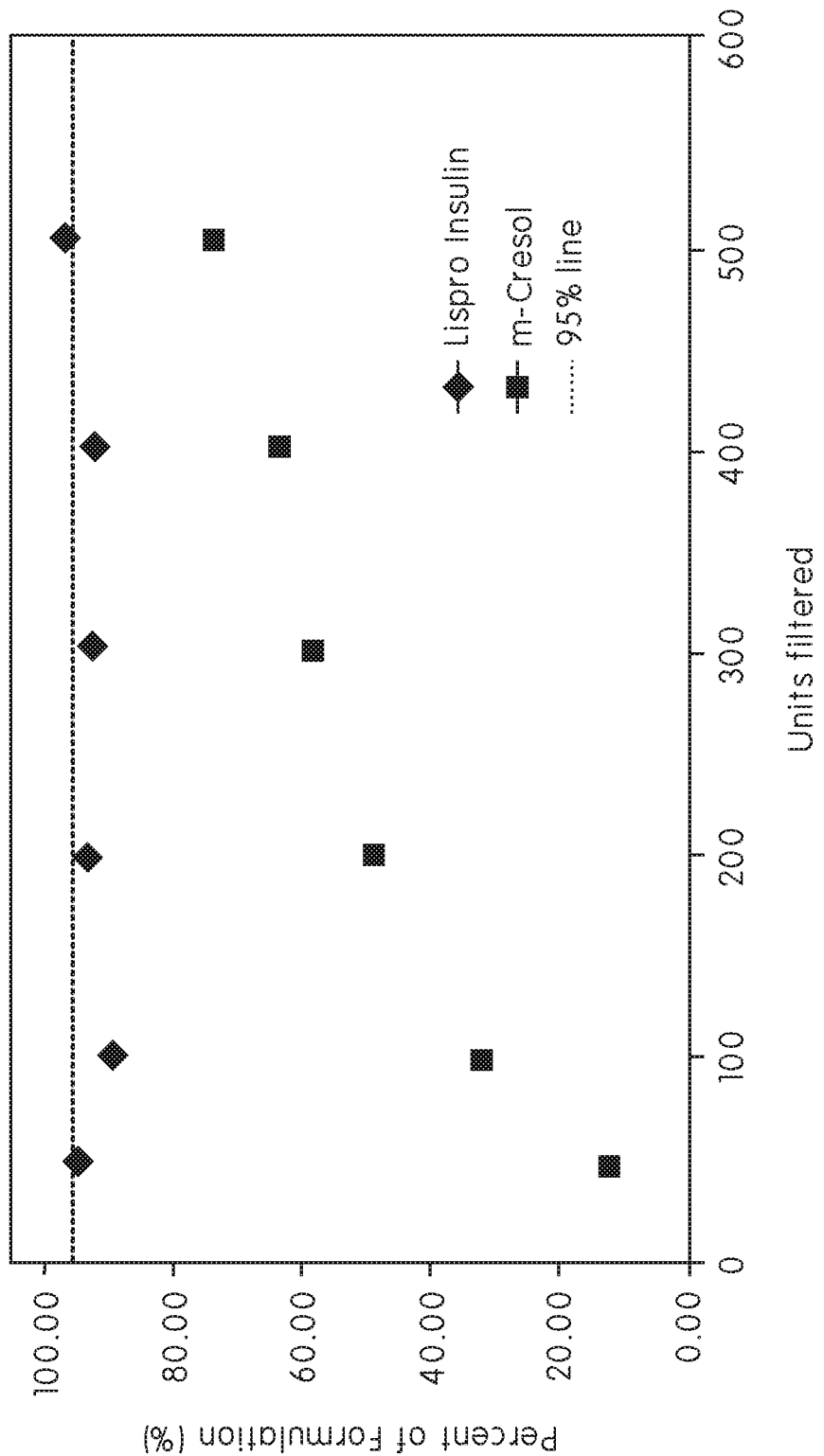
FIG. 13 shows efficacy of a resin in removing preservative/excipient and maintenance of insulin levels over repeated exposure to a commercial insulin preparation in accordance with an embodiment of the present invention.

Filtration may be accomplished by passing the pharmaceutical through a filtering device, such as, for example and without limitation, that illustrated in FIGS. 1-7, and the systems illustrated in FIGS. 8-10. As shown in FIG. 13, the Ambersorb resin became less efficacious at removing m-cresol over time, as more preservative was filtered by the resin. Insulin levels, in contrast, remained consistently high. These results show that protocols/methods for filtering pharmaceutical preparations will rely on contact time and resin use.

Figure 17:
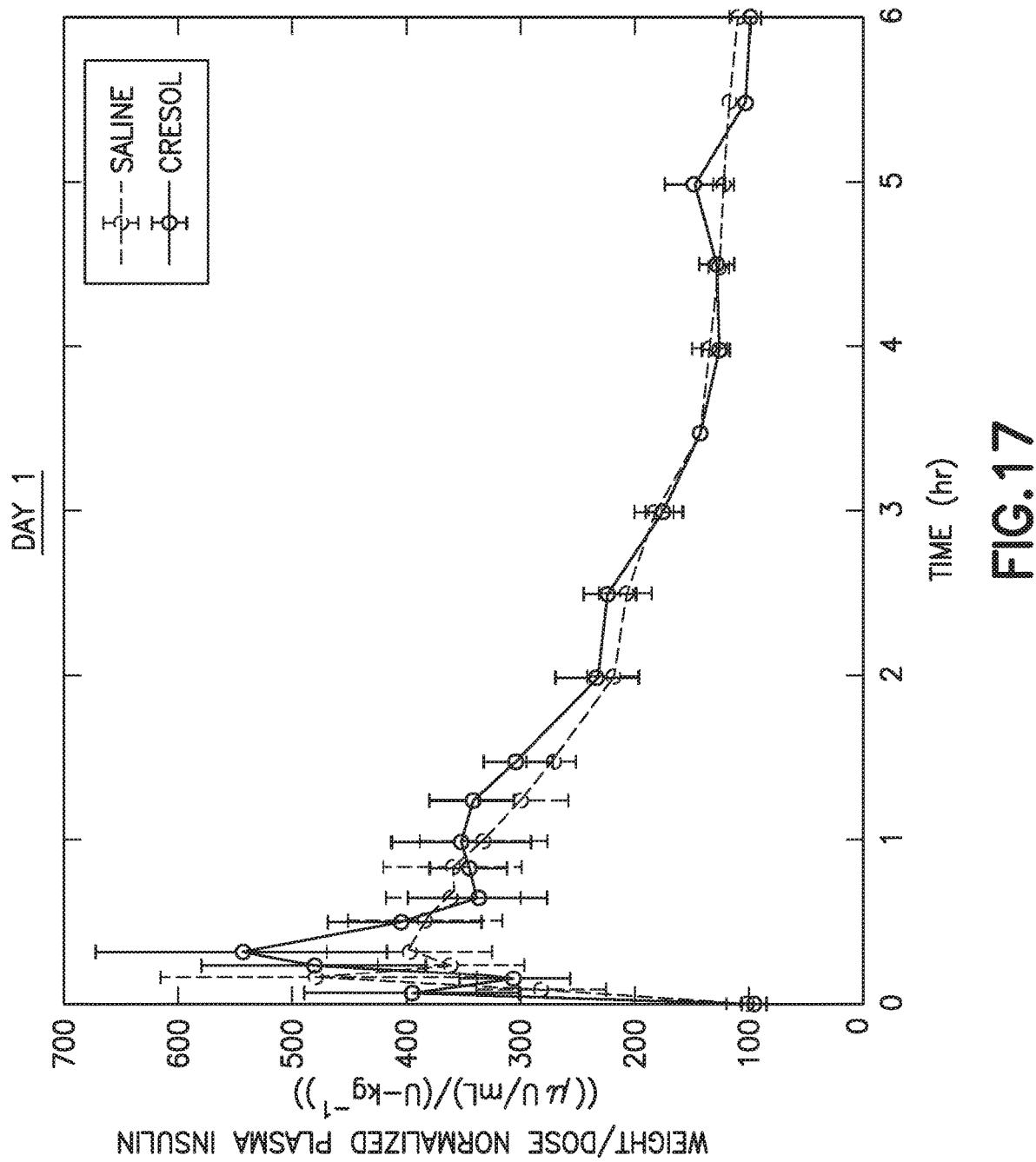
FIG. 17 is a graph showing the temporal effects of cresol exposure on subcutaneous insulin absorption at day 1.
Figure 18:
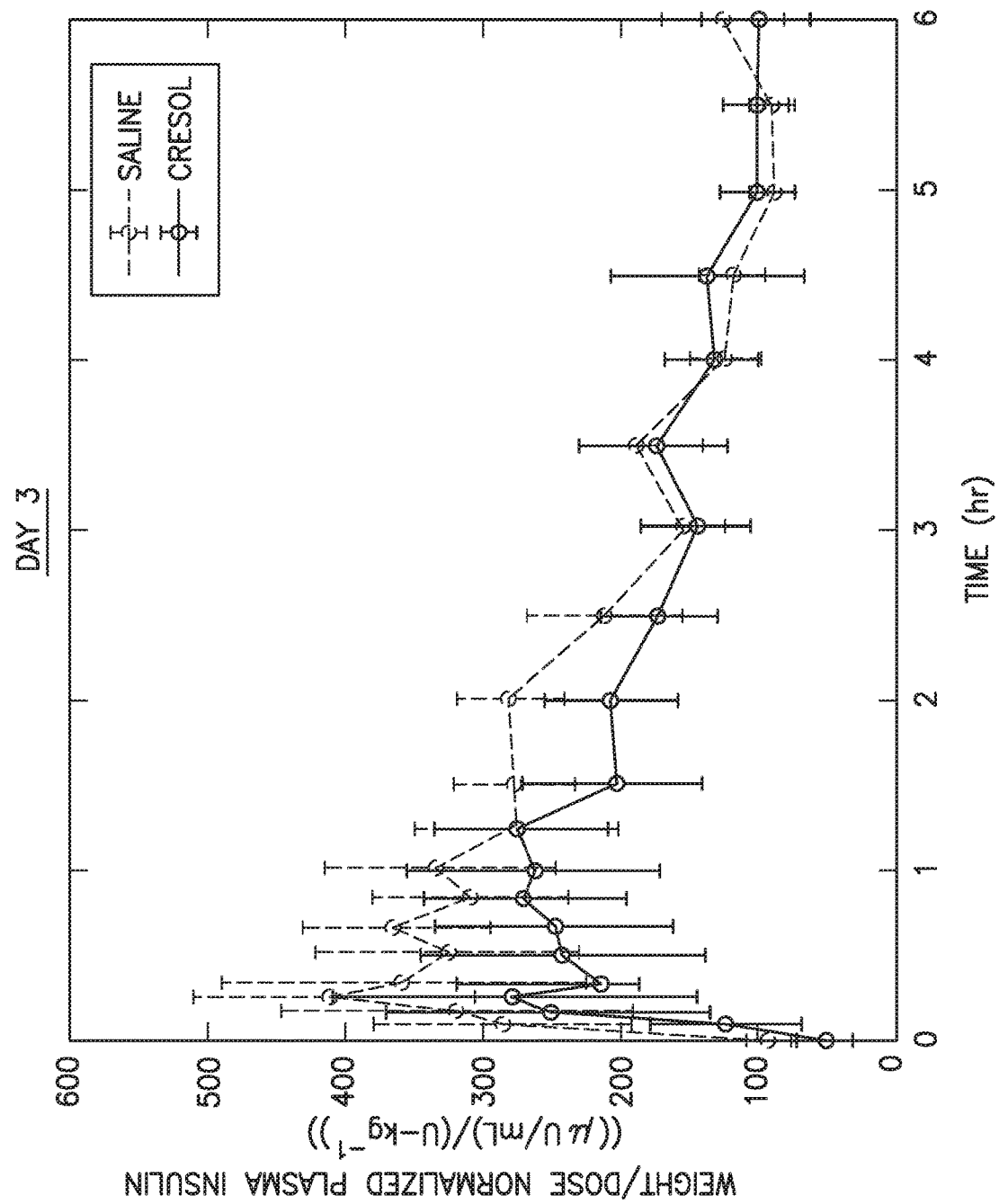
FIG. 18 is a graph showing the temporal effects of cresol exposure on subcutaneous insulin absorption at day 3.
Figure 19:
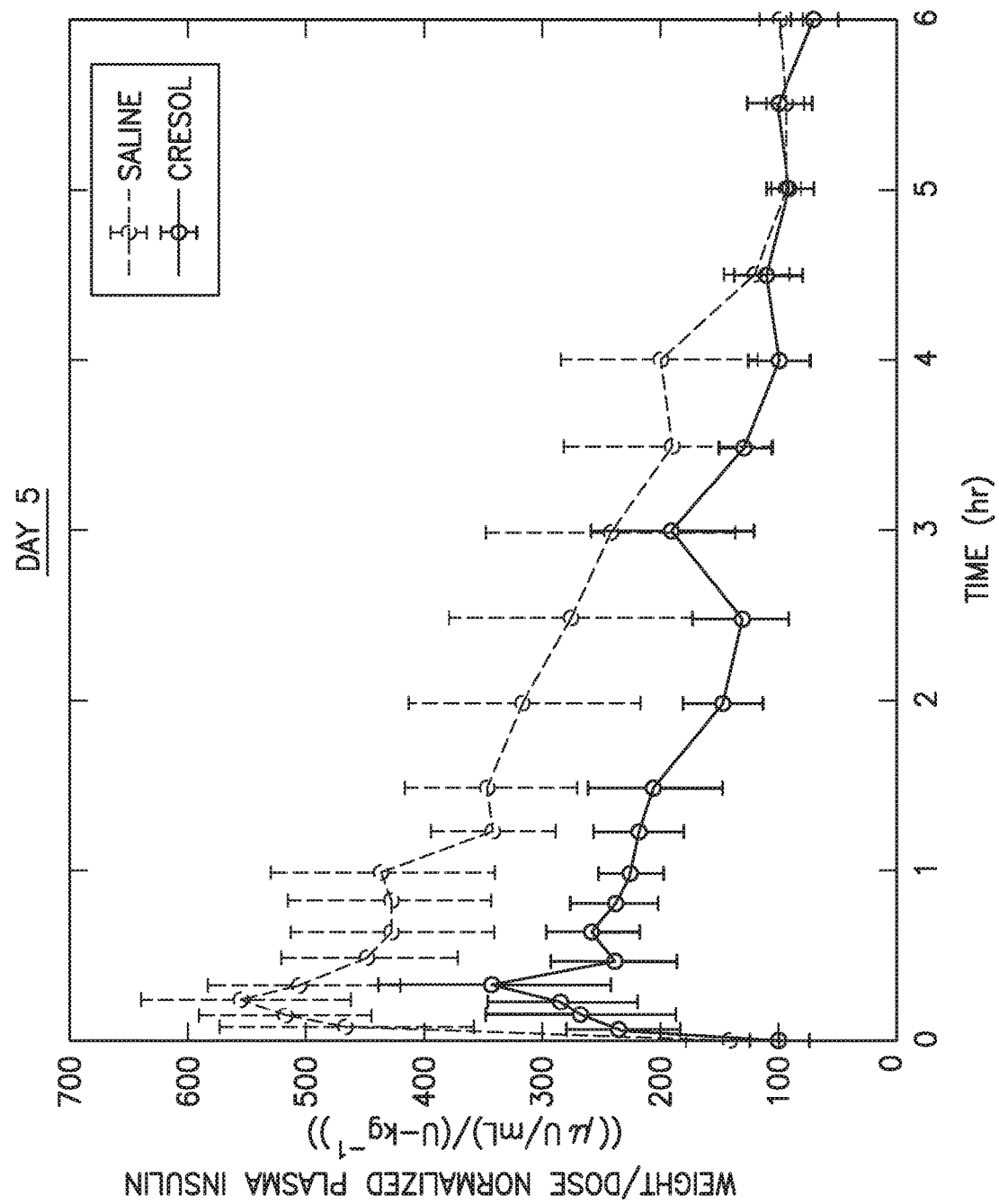
FIG. 19 is a graph showing the temporal effects of cresol exposure on subcutaneous insulin absorption at day 5.

With reference to FIGS. 17-19, a study was performed to determine the temporal effects of cresol exposure on subcutaneous insulin absorption. In this study, female Sinclair swine (n≥4) were subcutaneously infused with either saline or insulin formulation strength m-cresol (3.15 mg/mL) via a Roche Rapid D infusion set for five days. At Days 1, 3, and 5 of the infusion treatment, an insulin PK study was performed at the affected site via a 4 U subcutaneous bolus Humalog (insulin lispro) injection to assess local absorption. Blood was sampled periodically for six hours following injection, plasma separated and analyzed for Humalog content. Data were weight and dose normalized with individual points represented as cohort mean±standard error of the mean. FIG. 17 represents the effects of cresol exposure on subcutaneous insulin absorption at Day 1. FIG. 18 represents the effects of cresol exposure on subcutaneous insulin absorption at Day 3. FIG. 19 represents the effects of cresol exposure on subcutaneous insulin absorption at Day 5.

As shown in FIGS. 17-19, total insulin absorption, defined as the area under the plasma insulin v. time profiles, demonstrated a global trend (p<0.1) towards an effect from the m-cresol treatment. As shown in FIG. 19, the results at Day 5 demonstrate that cresol exposure could affect insulin absorption at times greater than 3 days. Accordingly, insulin formulation phenolic excipients reduce insulin absorption, thereby limiting effective wear times of insulin infusion catheters to a three day period. Filtration, accomplished by passing the pharmaceutical through a filtering device, such as, for example and without limitation, that illustrated in FIGS. 1-7, and the systems illustrated in FIGS. 8-10, may improve this result, as described herein.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A filtering device for removing a preservative from a pharmaceutical composition, the filtering device comprising:
a body having at least one inlet and at least one outlet and defining a fluid flow channel provided between the at least one inlet and at least one outlet, the fluid flow channel being in fluid communication with at least one chamber;
at least one resin disposed in the at least one chamber, wherein said resin is selected from the group consisting of polystyrene beads, polystyrene-divinyl benzene beads, and a resin that includes an activated carbon material; and
at least one filter disposed in the fluid flow channel having a pore size of about 15 μm to about 45 μm.

2. The device of claim 1, wherein the pharmaceutical composition is insulin.

3. The device of claim 2, wherein the preservative is a phenolic compound or derivative thereof.

4. The device of claim 3, wherein the resin is a plurality of said polystyrene-divinyl-benzene beads, and where said plurality of polystyrene beads are porous.

5. The device of claim 4, wherein the porous polystyrene-divinyl-benzene beads have a pore diameter of less than about 100 Å.

6. The device of claim 1, wherein the resin is a nonpolar compound.

7. The device of claim 1, wherein the resin is said polystyrene beads.

8. The device of claim 1, wherein the resin is said polystyrene-divinyl benzene beads.

9. The device of claim 1, wherein the resin is said resin that includes said activated carbon material.

10. The device of claim 1, wherein the at least one filter comprises a first filter and a second filter, and wherein the first filter and second filter are provided in the fluid flow channel on opposing sides of the chamber.

11. The device of claim 1, wherein the filter at least partially removes metal ion excipients from the pharmaceutical composition.

12. The filtering device of claim 1, further comprising a needle in communication with said at least one outlet of said fluid flow channel of said body, said needle configured for delivering the pharmaceutical composition to a patient.

13. The filtering device of claim 12, wherein said needle extends from a distal end of said body and said body has a proximal end with a threaded connection configured for coupling to a delivery device for the pharmaceutical composition.

14. A system comprising:
an injection device comprising
a housing defining a chamber configured to hold a medicament;
a displaceable plunger rod disposed at least partially within the housing, an actuator and spring disposed to advance said plunger rod upon actuation of said actuator; and
an outlet in fluid communication with the chamber; and
a filtering device comprising
a body having at least one inlet and at least one outlet and defining a fluid flow channel provided between the at least one inlet and at least one outlet, the fluid flow channel being in fluid communication with at least one chamber;
at least one resin disposed in the at least one chamber; and
at least one filter disposed in the fluid flow channel,
a needle attached to the outlet of said body;
wherein the outlet of the injection device is attached to the inlet of the filtering device such that the chamber of the injection device is in fluid communication with the fluid flow channel of the filtering device.

15. The system of claim 14, wherein the filtering device is removably attached to the injection device.

16. The system of claim 14, wherein the filter at least partially removes metal ion excipients from said medicament.

17. The system of claim 14, wherein the injection device comprises an infusion pump and the filtering device further comprises a needle attached to the outlet.

18. The system of claim 14, wherein the medicament is insulin.

19. The system of claim 14, wherein the resin of the filtering device comprises a nonpolar compound.

20. The system of claim 14, wherein the resin of the filtering device comprises polystyrene.

21. The system of claim 14, wherein the resin of the filtering device comprises divinyl benzene.

22. The system of claim 14, wherein the resin of the filtering device comprises a plurality of porous polystyrene-divinyl-benzene beads.

23. The system of claim 22, wherein the porous polystyrene-divinyl-benzene beads have a pore diameter of less than about 100 Å.

24. The system of claim 14, wherein the resin of the filtering device comprises a carbonaceous material.

25. A filtering device for removing a preservative from a pharmaceutical composition, the filtering device comprising:
  a body having at least one inlet and at least one outlet and defining a fluid flow channel provided between the at least one inlet and at least one outlet, the fluid flow channel being in fluid communication with at least one chamber;
at least one resin disposed in the at least one chamber; and
at least one filter disposed in the fluid flow channel, where said filter at least partially removes metal ion excipients from the pharmaceutical composition.

26. A system comprising:
an infusion pump comprising
a housing defining a chamber configured to hold a medicament;
an outlet in fluid communication with the chamber; and
a filtering device comprising
a body having at least one inlet and at least one outlet and defining a fluid flow channel provided between the at least one inlet and at least one outlet, the fluid flow channel being in fluid communication with at least one chamber;
a needle attached to said at least one outlet of said body configured for delivering the medicament;
at least one resin disposed in the fluid flow channel of said body; and
at least one filter disposed in the fluid flow channel,
wherein the outlet of the infusion pump is attached to the at least one inlet of the body of the filtering device such that the chamber of the housing of the infusion pump is in fluid communication with the fluid flow channel of the filtering device.

* * * * *